(12) United States Patent
Xie et al.

(10) Patent No.: US 12,097,500 B2
(45) Date of Patent: Sep. 24, 2024

(54) APPARATUS AND METHODS FOR MONITORING OF BIOMARKERS IN BLOOD

(71) Applicants: Rutgers, The State University of New Jersey, New Brunswick, NJ (US); The Trustees of the University of Pennsylvania, Philadelphia, PA (US)

(72) Inventors: Pengfei Xie, Piscataway, NJ (US); Mehdi Javanmard, West Windsor, NJ (US); Mark George Allen, Philadelphia, PA (US); Wen Shen, Arlington, TX (US); Naixin Song, Philadelphia, PA (US)

(73) Assignees: Rutgers, The State University of New Jersey, New Brunswick, NJ (US); The Trustees of the University of Pennsylvania, Philadelphia, PA (US)

( * ) Notice: Subject to any disclaimer, the term of this patent is extended or adjusted under 35 U.S.C. 154(b) by 282 days.

(21) Appl. No.: 16/852,113

(22) Filed: Apr. 17, 2020

(65) Prior Publication Data
US 2020/0261907 A1 Aug. 20, 2020

Related U.S. Application Data

(63) Continuation-in-part of application No. PCT/US2018/056718, filed on Oct. 19, 2018.
(Continued)

(51) Int. Cl.
*B01L 3/00* (2006.01)
*G01N 27/02* (2006.01)
*G01N 33/68* (2006.01)

(52) U.S. Cl.
CPC ............ *B01L 3/5085* (2013.01); *G01N 27/02* (2013.01); *G01N 33/6863* (2013.01);
(Continued)

(58) Field of Classification Search
CPC ..... B01L 2300/0636; B01L 2300/0645; B01L 2300/0893
(Continued)

(56) References Cited

U.S. PATENT DOCUMENTS

| 5,653,939 | A | * | 8/1997 | Hollis | ................. C12Q 1/6832 506/3 |
| 9,234,867 | B2 | | 1/2016 | Briman et al. | |

(Continued)

FOREIGN PATENT DOCUMENTS

| WO | 2016/100325 A1 | 6/2016 |
| WO | 2017/062591 A1 | 4/2017 |
| WO | 2019/190596 A1 | 10/2019 |

OTHER PUBLICATIONS

PCT International Search Report and Written Opinion for International Application No. PCT/US2018/056718 entitled "Transcutaneous Wearable Apparatus for Continuous Monitoring of Biomarkers In Blood," Mailed on Sep. 11, 2019, consisting of 16 pages.
(Continued)

*Primary Examiner* — Natalia Levkovich
(74) *Attorney, Agent, or Firm* — Hamilton, Brook, Smith & Reynolds, P.C.

(57) ABSTRACT

A sensor for detecting a target analyte in a sample includes a pair of conducting electrodes that are separated by a gap. An insulator is disposed in the gap between the electrodes. Plural wells are defined by one of the electrodes and the insulator, to expose the other of the electrodes. The wells are configured to receive a sample including a target analyte. The target analyte, when present in the sample received in the wells, modulates an impedance between the electrodes. The modulated impedance, which is measurable with an applied electrical voltage, is indicative of the concentration of the target analyte in the sample. The wells can include antibodies immobilized inside the wells, to bind the target
(Continued)

analyte, which can be a cytokine. Also provided are a method for label-free sensing of a target analyte in a sample, and a transcutaneous impedance sensor for label-free, in-situ biomarker detection.

17 Claims, 26 Drawing Sheets
(3 of 26 Drawing Sheet(s) Filed in Color)

Related U.S. Application Data

(60) Provisional application No. 62/575,254, filed on Oct. 20, 2017.

(52) U.S. Cl.
CPC ............ *B01L 2300/0636* (2013.01); *B01L 2300/0645* (2013.01); *B01L 2300/0893* (2013.01); *B01L 2300/123* (2013.01)

(58) Field of Classification Search
USPC .................................................. 422/552, 554
See application file for complete search history.

(56) References Cited

U.S. PATENT DOCUMENTS

| | | | |
|---|---|---|---|
| 2004/0072357 A1 | 4/2004 | Stiene et al. | |
| 2005/0052646 A1* | 3/2005 | Wohlstadter | B01L 9/50 356/311 |
| 2014/0012114 A1* | 1/2014 | Zevenbergen | A61B 5/14517 600/346 |
| 2014/0147336 A1 | 5/2014 | Ching et al. | |
| 2014/0249435 A1 | 9/2014 | Banet et al. | |

OTHER PUBLICATIONS

Mahmoodi, Seyed Reza et al., "Multiwell Plate Impedance Analysis of a Nanowell Array Sensor for Label-Free Detection of Cytokines in Mouse Serum," IEEE Sensors Letters, vol. 4, No. 2, (Feb. 2020).

Daniels, Jonathan, et al., "Label-Free Impedance Biosensors: Opportunities and Challenges," Electroanalysis 19(12):1239-1257 (May 2007).

Xie, Pengfei et al., "Nanowell Array Imedance Sensor for Label-Free Quantification of cytokines in Serum . . . " MicroTAS (2017).

Shen, Wen, et al., "Extracellular matrix-based intracortical microelectrodes: Toward a microfabricated neural interface based on natural materials," Microsystems and Nanoengineering 1, 15010 (2015).

Emaminejad, S., et al., "Microfluidic diagnostic tool for the developing world: Contactless impedance flow cytometry," Lab Chip. Author manuscript; available in PMC Nov. 7, 2013. pp. 1- 16, Published in final edited form as Lab Chip 12(21) 4499-4507 (2012).

International Preliminary Report on Patentability, for Int. Appl. No. PCT/US2018/056718, entitled, "Transcutaneous Wearable Apparatus for Continuous Monitoring of Biomarkers In Blood," date of Mailing: Apr. 21, 2020.

* cited by examiner

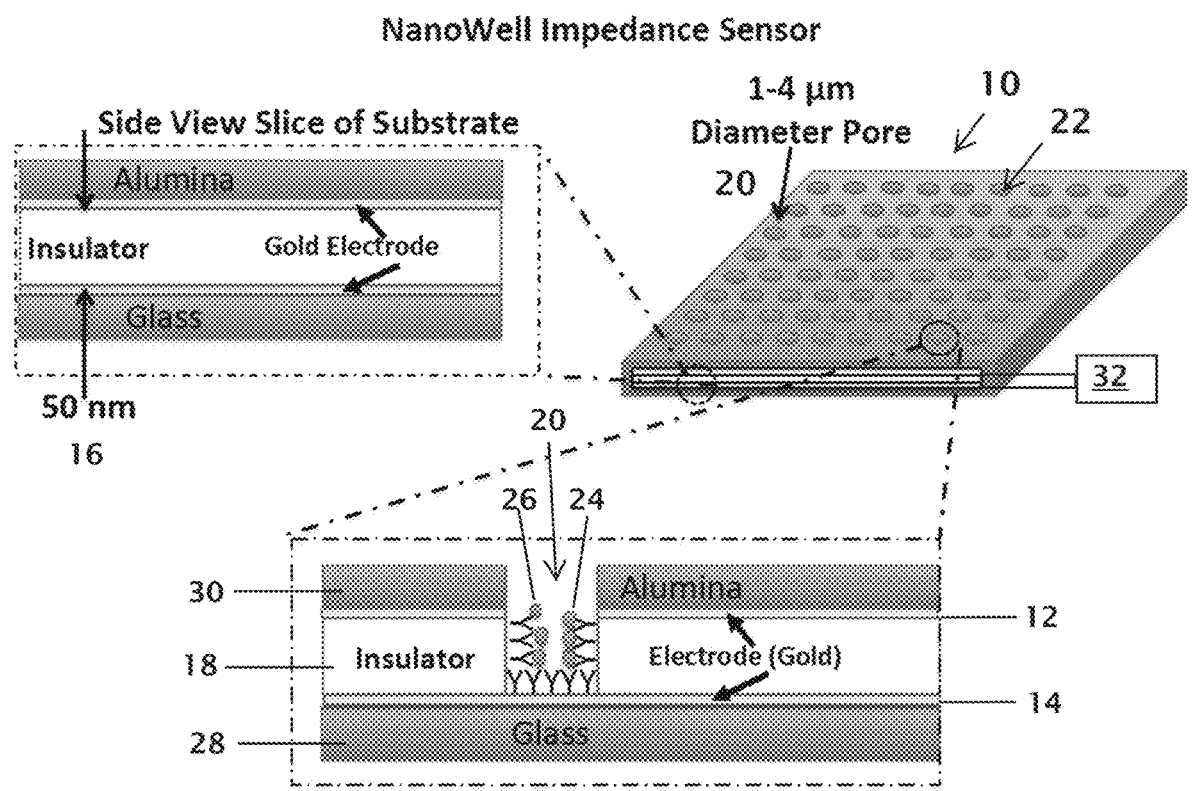
FIG. 1
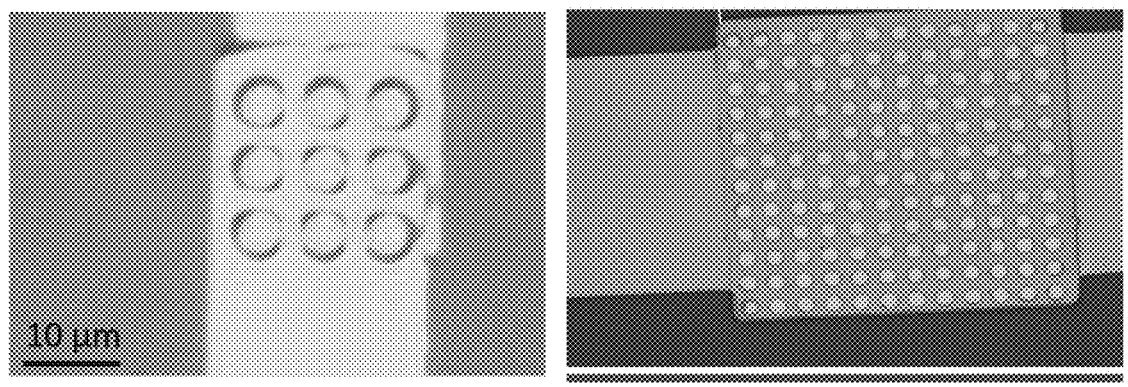
FIG. 2A                    FIG. 2B

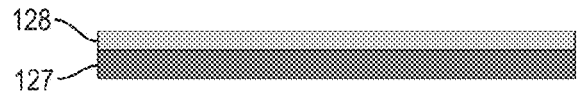
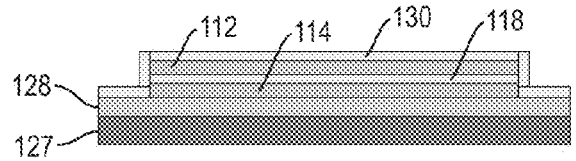
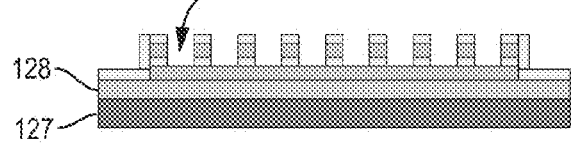
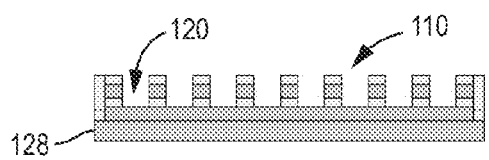
FIG. 7A
FIG. 7B
FIG. 7C
FIG. 7D
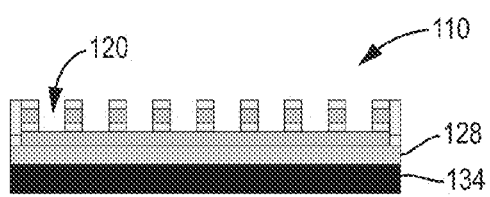
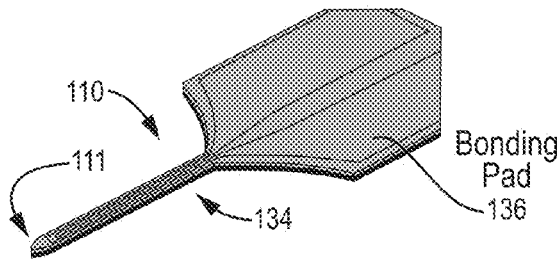
FIG. 7E
FIG. 7F
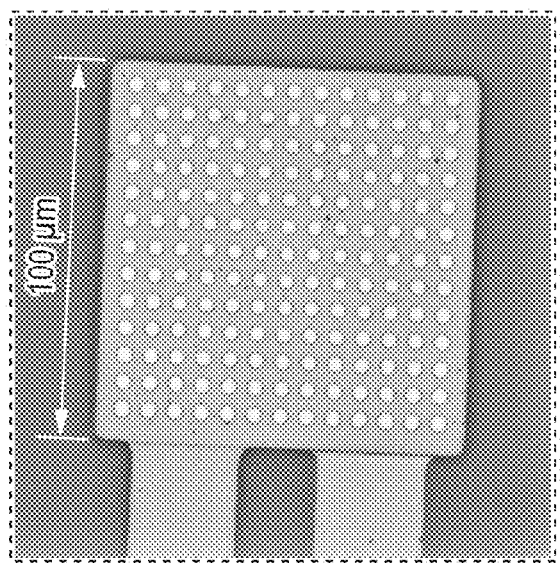
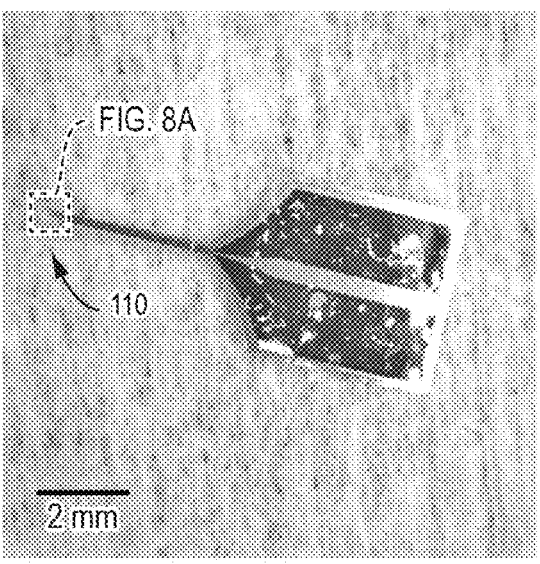
FIG. 8A
FIG. 8B

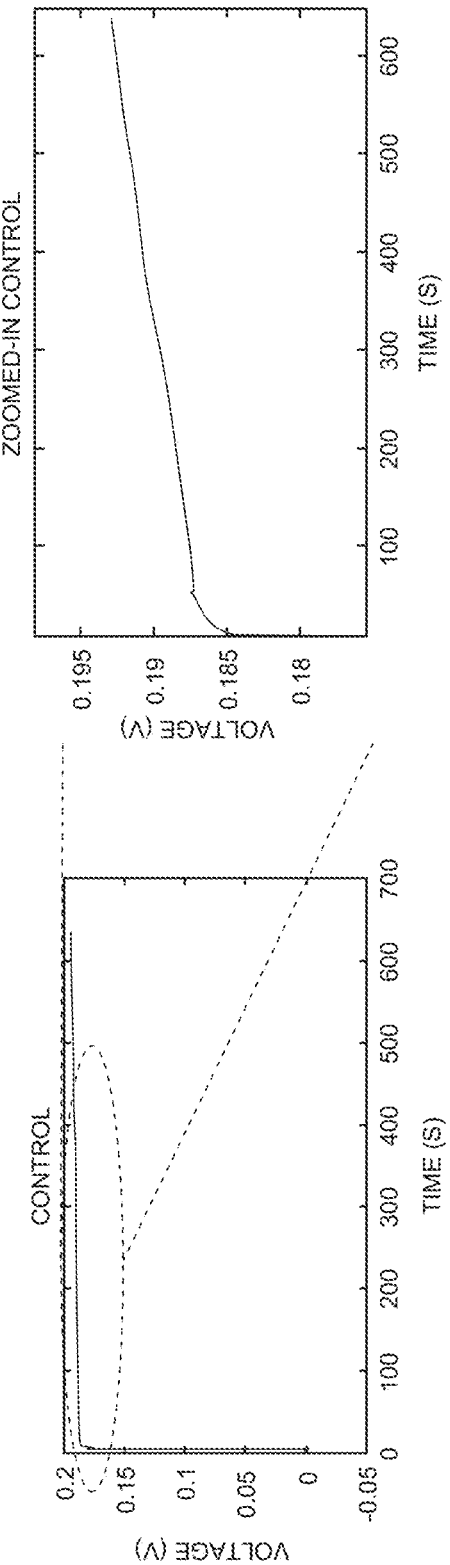
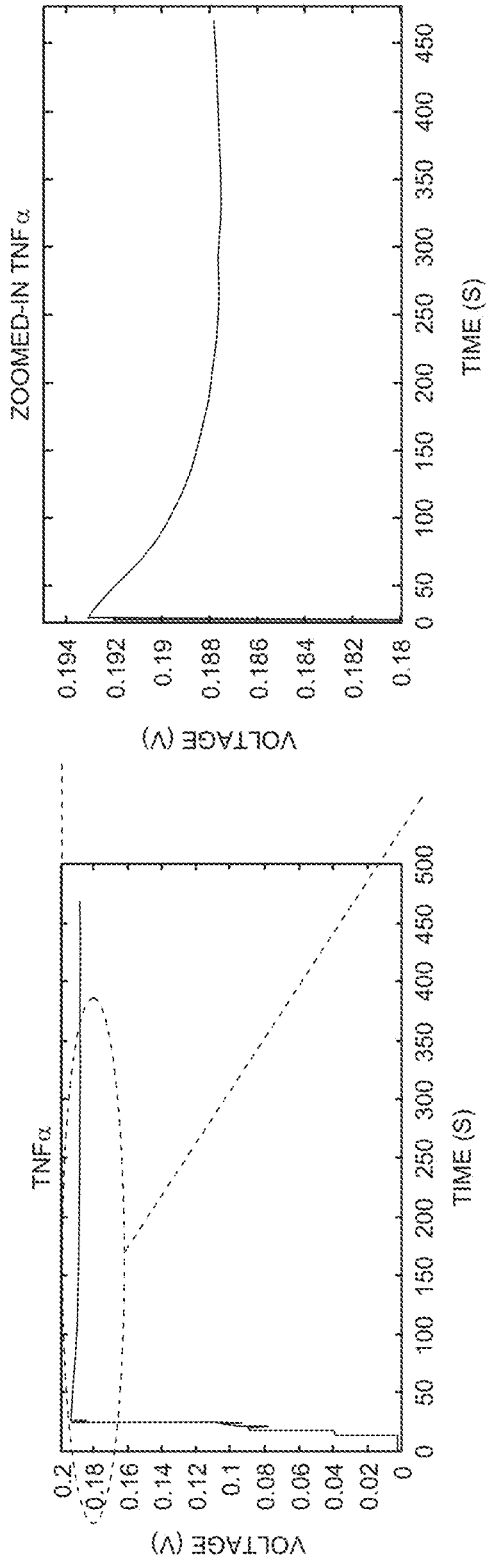
FIG. 15B
FIG. 15D
FIG. 15A
FIG. 15C

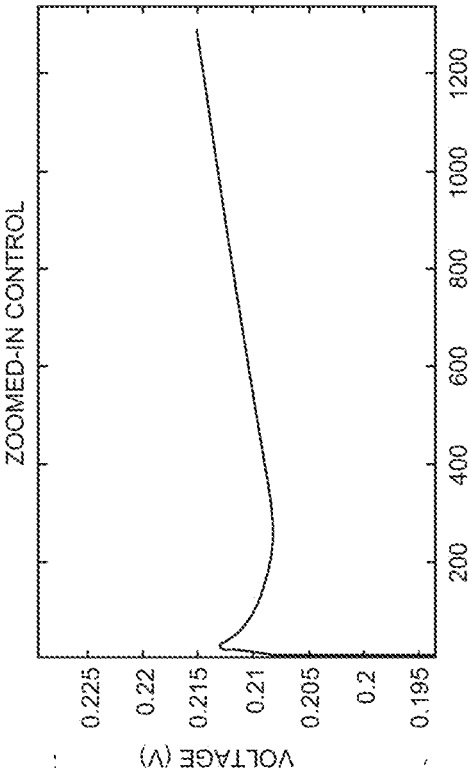
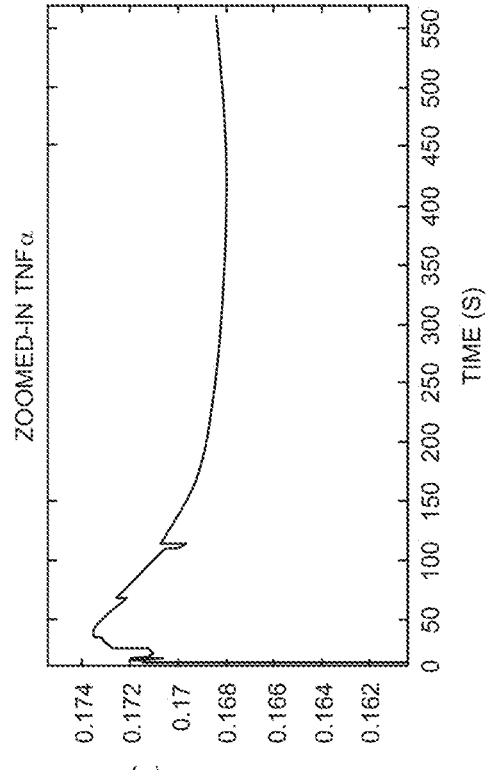
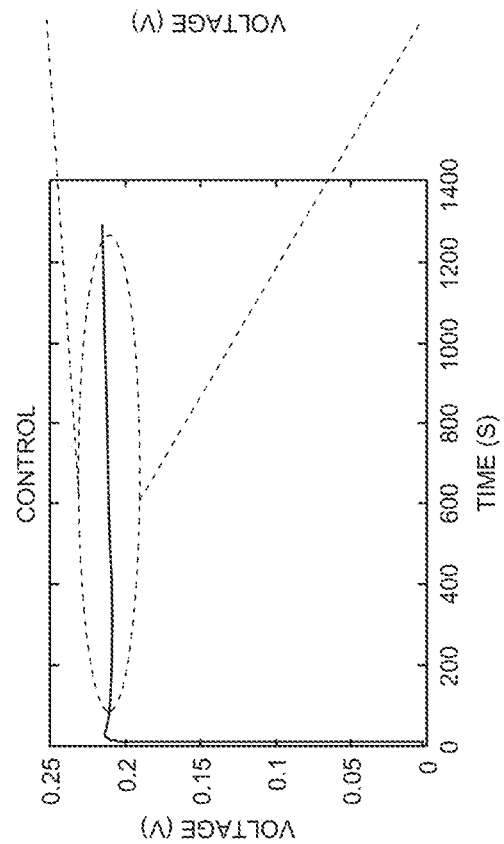
FIG. 16A  FIG. 16B  FIG. 16C  FIG. 16D

APPARATUS AND METHODS FOR MONITORING OF BIOMARKERS IN BLOOD

RELATED APPLICATIONS

This application is a continuation-in-part of International Application No. PCT/US2018/056718, filed Oct. 19, 2018, which claims the benefit of U.S. Provisional Application No. 62/575,254 filed on Oct. 20, 2017. The entire teachings of the above applications are incorporated herein by reference.

GOVERNMENT SUPPORT

This invention was made with government support under HR011-16-2-0026 from DARPA. The government has certain rights in the invention.

BACKGROUND

The ability to measure proteins or other biomarkers in bodily fluids, e.g., blood, can enable continuous health monitoring. The gold-standard technique for protein quantification is ELISA, which typically relies on optical fluorescence and labeling that result in lengthier and more costly test procedures.

SUMMARY

A sensor for detecting a target analyte in a sample includes a pair of conducting electrodes that are separated by a gap. An insulator is disposed in the gap between the electrodes. Plural wells are defined by one of the electrodes and the insulator, to expose the other of the electrodes. The wells are configured to receive a sample including a target analyte. The target analyte, when present in the sample received in the wells, modulates an impedance between the electrodes, the modulated impedance being measurable with an applied electrical voltage. The modulated impedance is indicative of the concentration of the target analyte in the sample.

The term "analyte" as used herein means a protein, peptide, and more specifically a cytokine (e.g., TNF-α, IL-1, IL-4, IL-6, IL-8, IL-10, IL-13) and other biomarkers (e.g., tumor biomarkers and other proteins known to link to diseases), hormones (e.g., insulin, cortisol), nucleic acids, toxins, small molecules, and any substances that can bind to a probe molecule. Cytokines are a broad category of small proteins (~5-20 kDa) that are important in cell signaling.

The wells (also referred to herein as pores) can be configured to bind the target analyte. For example, the wells can include antibodies immobilized inside the wells, to bind the target analyte. In an embodiment, the target analyte is a protein (e.g., a cytokine) and the sample is serum (e.g., from mammalian blood).

Alternatively or in addition, the wells can include aptamers immobilized inside the wells, to bind the target analyte. Aptamers (e.g., oligonucleotide or peptide molecules) can be used to capture target analytes (e.g., proteins, peptides, small molecules).

The electrodes can be parallel plates. The electrodes can overlap to form an overlapping region, the wells being defined within the overlapping region.

In an embodiment, the electrodes are gold electrodes and the insulator comprises aluminum oxide.

The electrodes and the insulator can be fabricated on a substrate. The substrate can flexible. Suitable materials for the substrate include parylene and other flexible, biocompatible materials.

The electrode that defines the wells (e.g., the upper electrode) can be covered with a protective layer. In an example, the protective layer can be formed from alumina. In embodiments, the protective layer covers portions of the wells. The protective layer can be configured to sequentially unveil the portions of the wells for continuous monitoring of the analyte. Unveiling can be accomplished through an electromechanical process to remove (e.g., burn off, melt away, etc.) portions of the protective layer, as further described herein.

The wells can be substantially cylindrical. A diameter of each well can be in the range of about 1 micrometer to about 4 micrometers. The wells can be arranged in a regularly spaced array.

The sensor can further include circuitry coupled to the electrodes, the circuitry applying the electrical voltage to the sample in the wells via the electrodes and measuring a current via the electrodes in response to the voltage applied. The modulated impedance between the electrodes can be determined as a function of the voltage applied and the current measured.

The voltage applied (or current applied) to the electrodes can be a time varying signal. The modulated impedance can be determined at a frequency in the range of about 50 kHz to about 10 Mhz. In an embodiment, the modulated impedance is determined at about 1 MHz.

The circuitry can include a lock-in amplifier.

A method for label-free sensing of a target analyte in a sample includes providing a sensor, wherein the sensors includes: a pair of conducting electrodes, the electrodes separated by a gap; an insulator disposed in the gap between the electrodes; and plural wells defined by one of the electrodes and the insulator, to expose the other of the electrodes. The method further includes receiving a sample in at least a portion of the wells and measuring impedance between the electrodes to determine modulated impedance due to a target analyte being present in the sample received in the wells, the modulated impedance being indicative of the concentration of the target analyte in the sample.

Measuring the modulated impedance can include applying an electrical voltage to the electrodes.

The method can further include binding the analyte within the wells. Binding the analyte can include using antibodies functionalized (e.g., immobilized) in the wells to capture the analyte.

Multiple sensors can be provided. Portions of the sensors can be covered by a protective layer, which can be selectively melted away to sequentially unveil the portions of the sensors for continuous monitoring of the analyte. For example, the protective layer can be a membrane, and the membrane can be selectively melted away (e.g., burned off) by applying a voltage to a portion of the membrane to cause that portion of the membrane to melt. While the membrane is being melted, impedance of one of the sensors that is covered by the membrane can be monitored. Application of the voltage to the membrane can be stopped when a drop in the impedance of the sensor is detected.

A transcutaneous impedance sensor for label-free, in-situ detection of a target analyte includes a flexible sensor and an insertion device to insert the flexible sensor through skin into the biological body. The flexible sensor includes a flexible substrate, a pair of conducting electrodes supported by the flexible substrate and separated by a gap, an insulator disposed in the gap between the electrodes, and an array of wells defined by at least one of the electrodes and the insulator, to expose the other of the electrodes. The wells are configured to receive a biological fluid sample (e.g., blood, serum from blood) including a target analyte (e.g., a cytokine). Antibodies are immobilized inside the wells. Binding of the target analyte, when present in the biological fluid sample received in the wells, modulates an impedance between the electrodes, the modulated impedance being measurable with an applied electrical voltage, the modulated impedance being indicative of the concentration of the target analyte in the sample.

The insertion device can be manufactured from metal (e.g., stainless steel) or other suitable material that lends the device sufficient stiffness for the application. The insertion device can include a needle-shaped tip, having a sharp point to facilitate insertion into tissue. The insertion device and the flexible sensor can cooperate to position the array of wells near the needle-shaped tip.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 1 is a schematic illustration of a NanoWell array, label-free impedance sensor according to an example embodiment of the invention. Electrodes in the array monitor impedance in the well. As protein binds to antibodies functionalized in the well, a rise in impedance is observed between electrodes.

FIGS. 2A and 2B are microscopic images of microfabricated sensors of differing sizes and different array size and density.

FIG. 3A illustrates sensor response with respect to time as monoclonal antibody (anti-Leptin IgG) physically adsorbs in the well(s) of the sensor resulting in exponential drop in baseline. FIG. 3B illustrates sensor response with respect to time as leptin in solution binds to electrode surface functionalized with anti-leptin IgG resulting in 4.37% drop in current across electrodes. FIG. 3C illustrates sensor response to a negative control. When blank Phosphate Buffer Saline (PBS) sample is added in fluidic well containing sensor, aside from initial baseline shift common to all steps, current across electrodes generally rises by 1%. This is seen with all negative control experiments and is likely due to antibody desorption.

FIGS. 7A-7F are schematic illustrations of a process for fabricating the flexible sensor of FIG. 6. FIGS. 7A-7E are cross sectional views of the micro-sized wells formed at the sensor tip. FIG. 7F is a 3-D view of the sensor, including the needle-shape tip and the wider section having the contact pads for coupling the sensor electrodes to circuitry for impedance measurements.

FIGS. 8A and 8B are microscopic images of example fabricated flexible sensors. FIG. 8A shows a sensor before detaching from a wafer. FIG. 8B shows a sensor after the alignment with stainless steel insertion device.

FIG. 9A illustrates adding PBS in fluidic cell increases ions transfer between two electrodes, which results in a decrease in impedance.

FIG. 9B illustrates that, as antibodies being physically adsorbed with time, the sensor responds with an increase in impedance.

FIG. 10A is a schematic illustration of the configuration of the skin phantom includes epidermis (PDMS), dermis and hypodermis (8 wt % gelatin gel), and blood vessel (fluidic channel with dyed PBS solution).

FIG. 10B illustrates insertion, assisted with a stainless-steel insertion device, of the flexible sensor through the skin phantom and into the fluidic channel.

FIGS. 10C and 10D illustrate removal of the stiff backing, leaving the flexible sensor intact in the skin phantom.

FIG. 11A illustrates that after the insertion of flexible sensor through skin phantom into fluidic cell, physical immobilization of anti-TNF-α on the sensor surface results in a drop in the current across the electrodes. The current across the electrode is determined from the output voltage (shown in FIG. 11A) by dividing the output voltage by amplifier gain. Input voltage divided by current is equal to impedance.

FIG. 11B illustrates that adding blank PBS into a fluidic well as a negative control generally increases the baseline.

FIG. 11C illustrates specific binding of TNF-α to anti-TNF-α results in a drop in current aside from initial baseline shift.

deposit graphene using PDMS stamping method or reduced graphene oxide (RGO) using a modified dropcast method, 5) photo-pattern graphene/RGO; 6) atomic layer deposition of Silicon Dioxide and deposition of graphene/RGO; 7) photo-pattern graphene/RGO; 8) photo-pattern and etch micro-needles using deep RIE or ion milling; 9) using photopatterning and angled sputtering, deposit gold at the side of the needle to provide electrical contact to the top graphene electrode layer; and 10) use atomic layer deposition to coat the needle and sensor with an oxide layer, and photo-pattern nanoscale pores through the graphene sensor using a stepper.

FIGS. 15A-15D are plots of output voltage as a function of time illustrating sensor response after immobilization, drying, and then addition of test sample. FIG. 15A shows the sensor response to a negative control. FIG. 15B shows a zoomed-in region of FIG. 15A.

FIG. 15C illustrates the sensor response to TNF-α, with FIG. 15D showing a zoomed-in portion of FIG. 15C.

FIGS. 16A-16D are plots of output voltage as a function of time illustrating sensor response after immobilization, drying, 2-day storage, addition of test sample. FIG. 16A shows the sensor response to a negative control and FIG. 16B shows a zoomed-in region of FIG. 16A. FIG. 16C illustrates the sensor response to TNF-α, with FIG. 16D illustrating a zoomed-in portion of FIG. 16C.

Figure 17A:
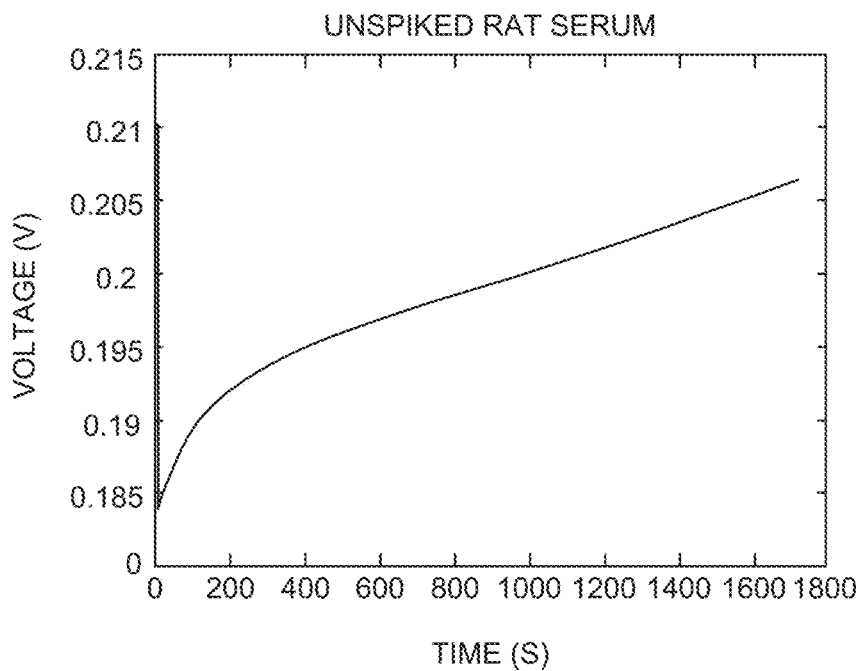
Figure 17B:
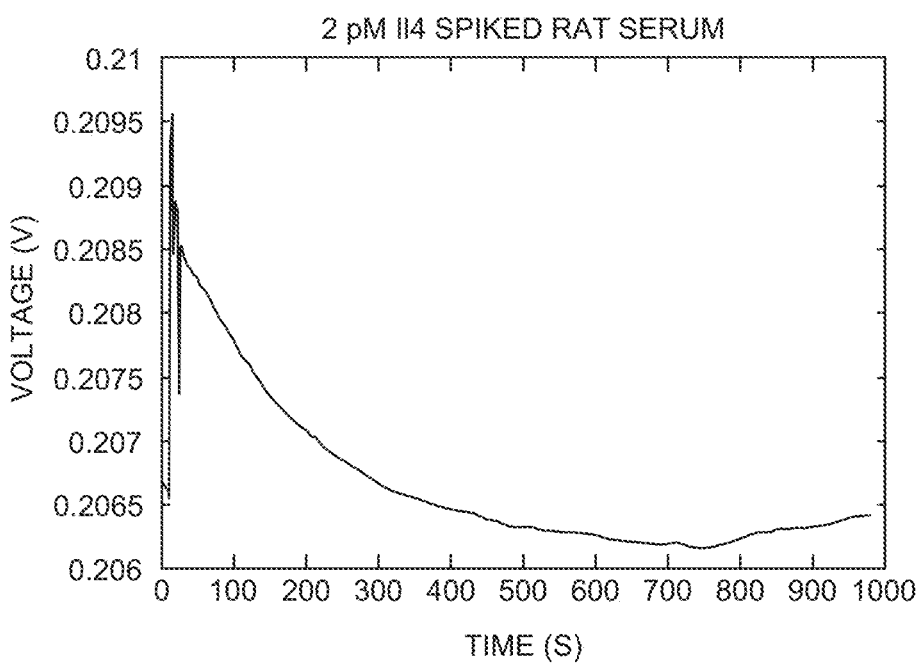

FIGS. 17A and 17B are plots of output voltage as a function of time illustrating sensor response to unspiked rat serum (FIG. 17A) and rat serum spiked with 2 pM 114 (FIG. 17B).

Figure 18A:
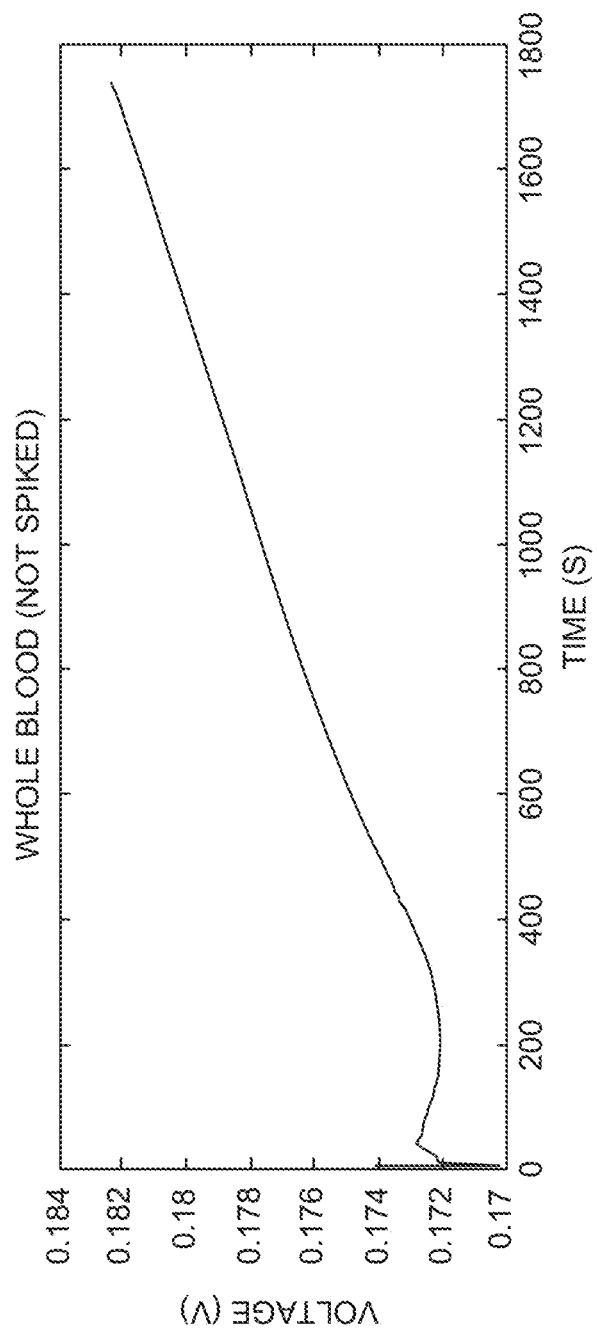
Figure 18B:
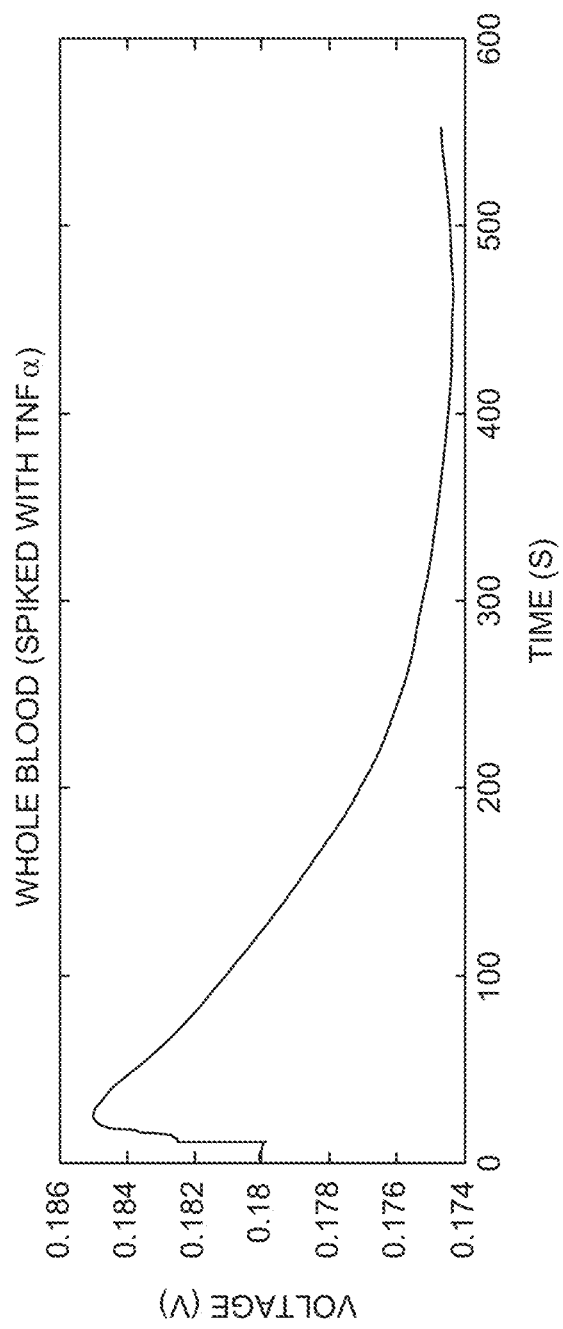

FIGS. 18A and 18B are plots of output voltage as a function of time illustrating sensor response to unspiked whole blood (FIG. 18A) and whole blood spiked with TNF-α (FIG. 18B).

Figure 19:
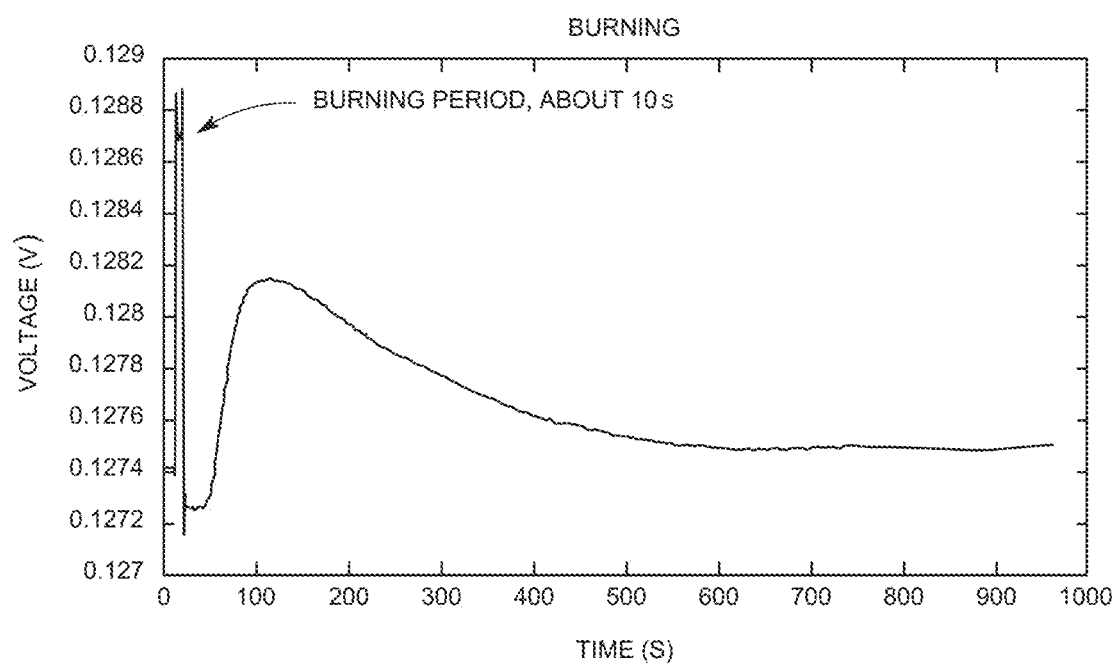

FIG. 19 is a plot of output voltage as a function of time illustrating sensor response for continuous monitoring including burning of membrane that initially covers the sensor.

Figure 20:
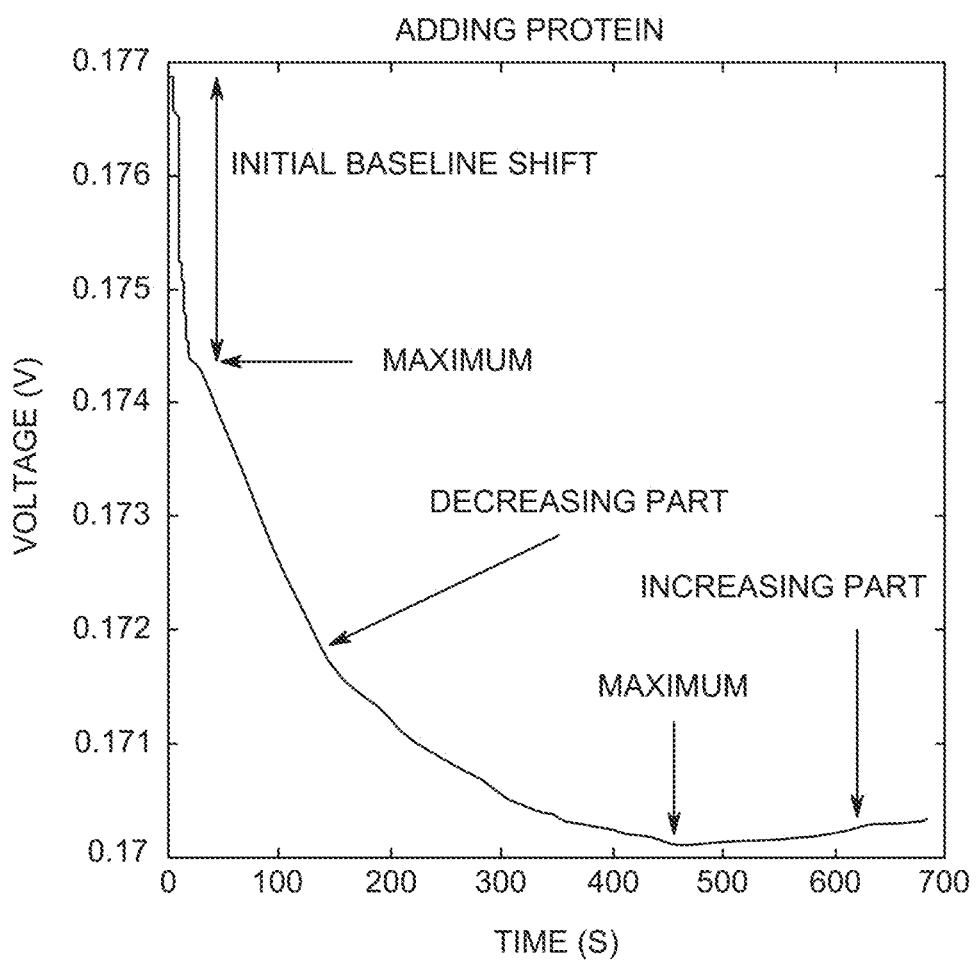

FIG. 20 illustrates feature extraction from the voltage vs. time curve for automatic analysis of sensor data.

Figure 21:
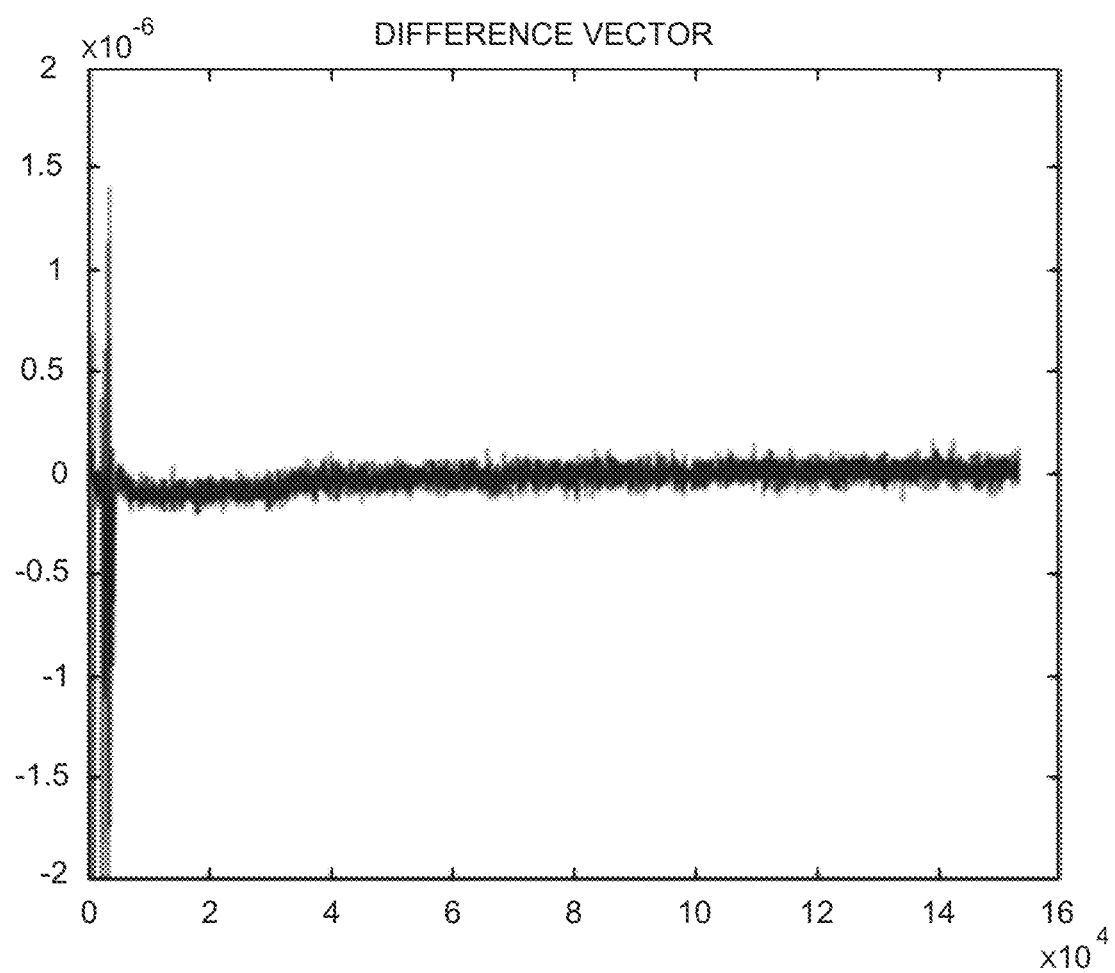

FIG. 21 illustrates example data for difference vector processing.

Figure 22A:
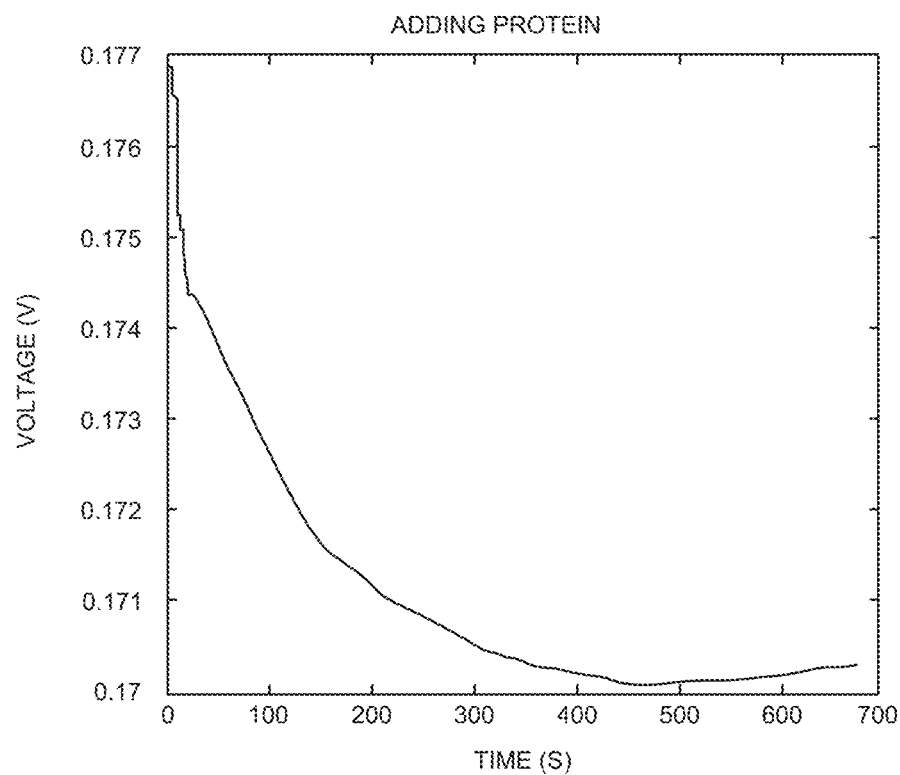
Figure 22B:
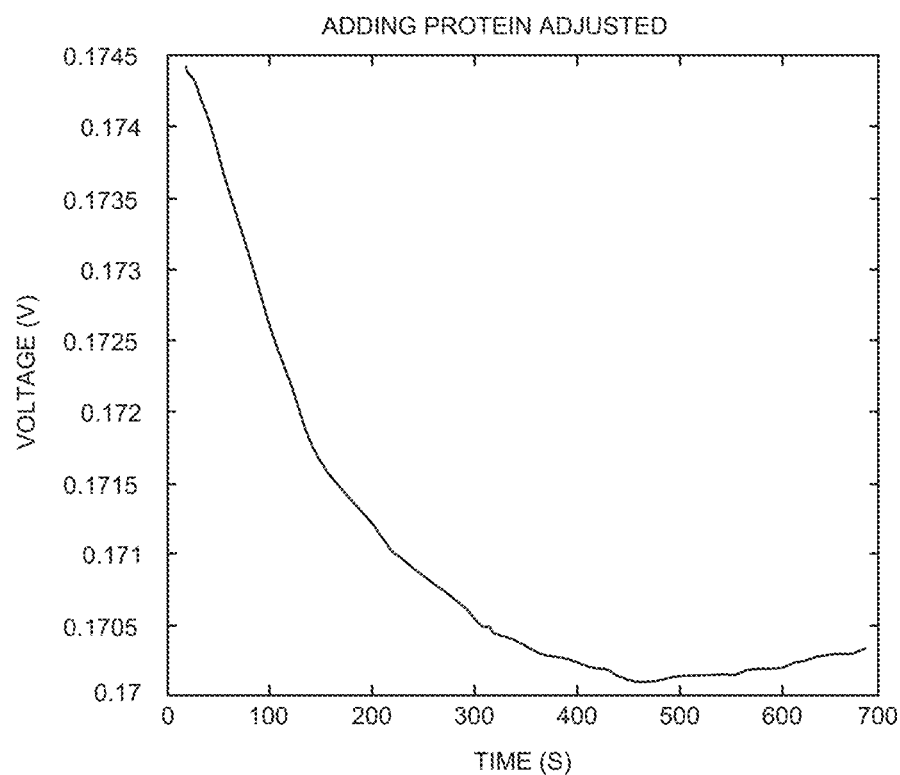

FIGS. 22A and 22B illustrate removing baseline shift.

Figure 23:
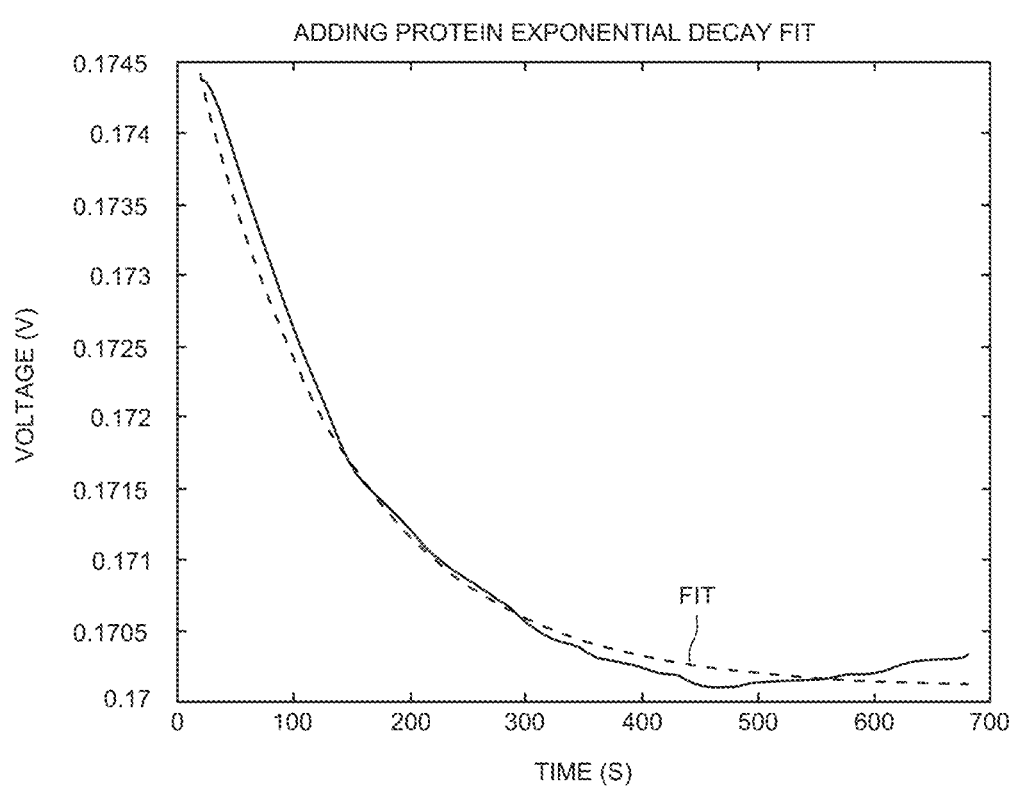

FIG. 23 illustrates the data of FIG. 22B and an exponential decay fit to the data.

Figure 24:
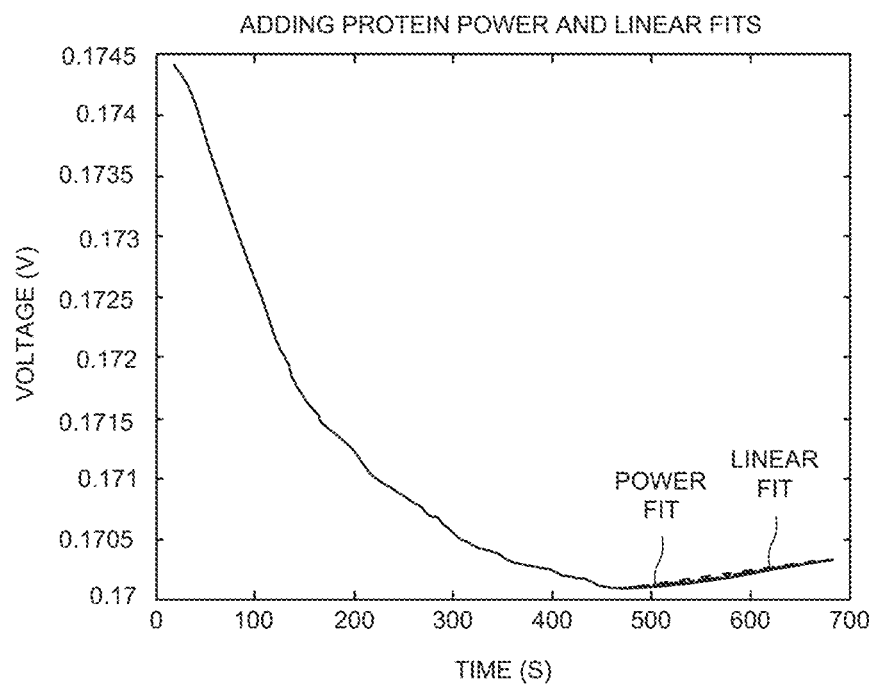

FIG. 24 illustrates specific binding data, here the protein data of FIG. 23, superimposed with a power fit and a linear fit at the end regions (increasing region).

Figure 25:
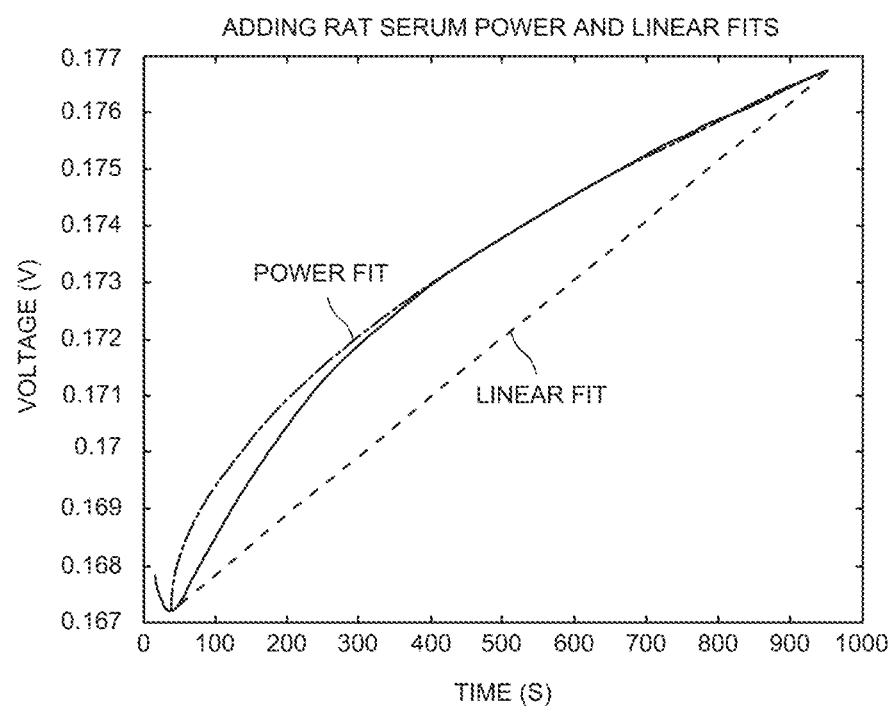
Figure 26A:
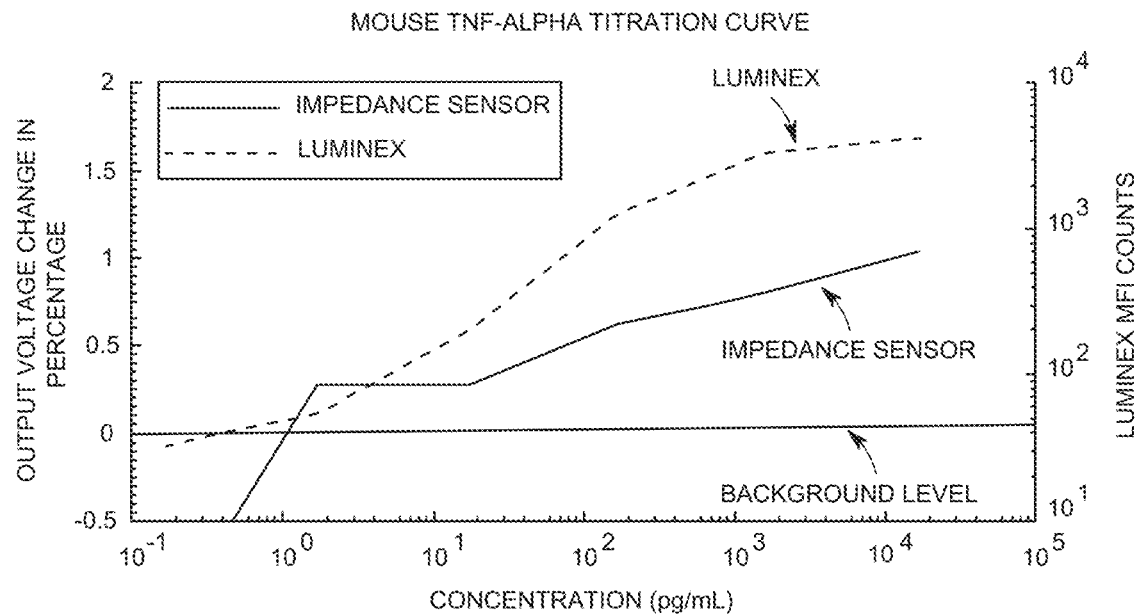
Figure 26B:
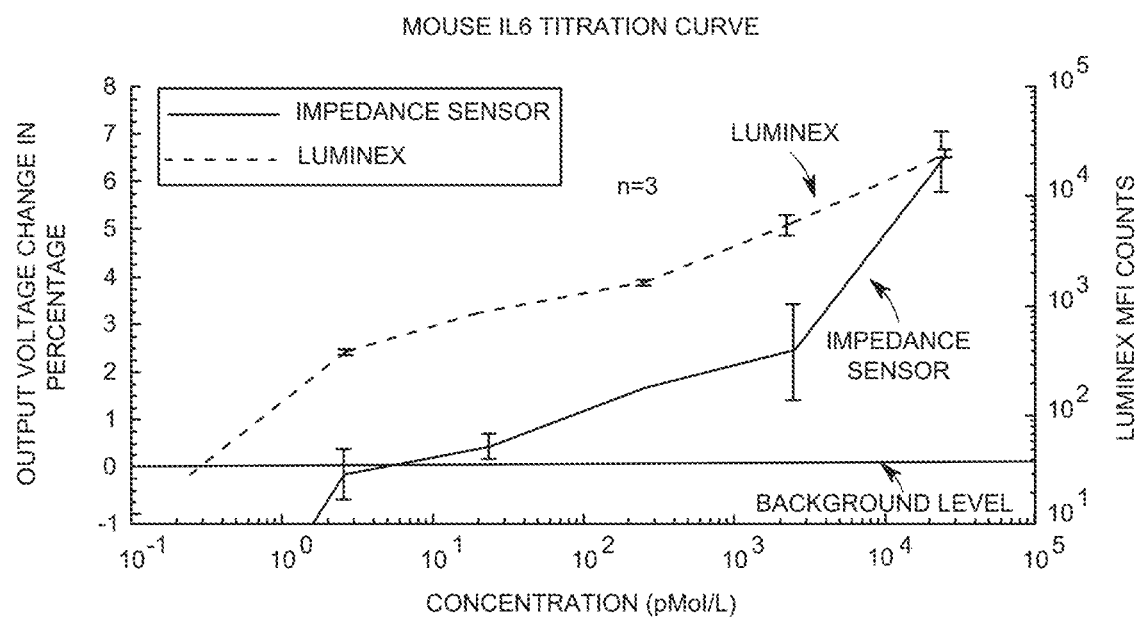
Figure 26C:
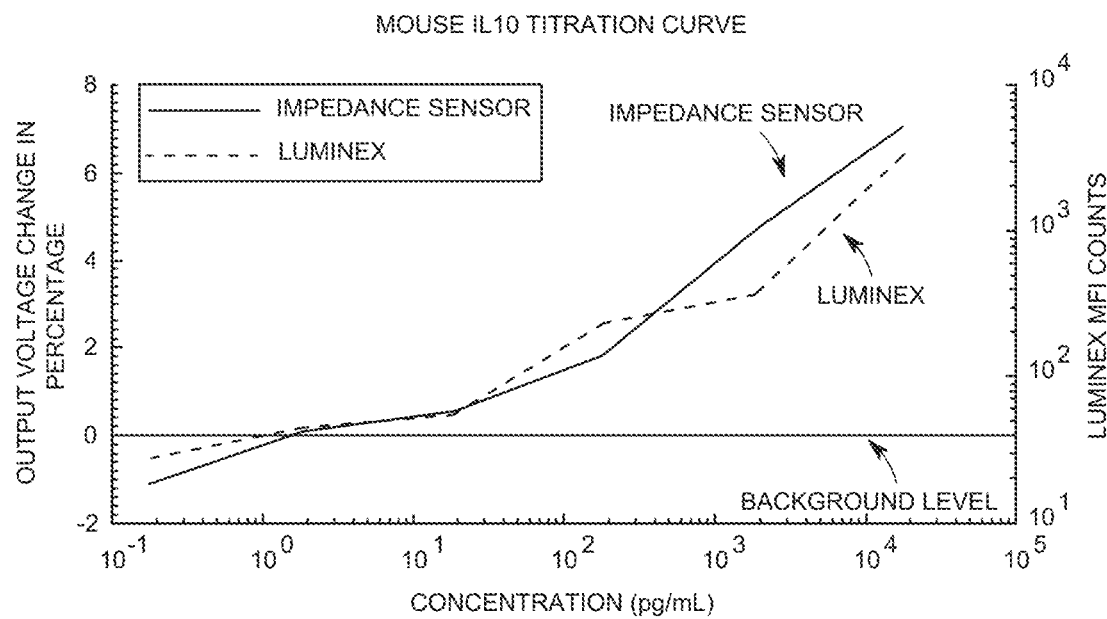
Figure 26D:
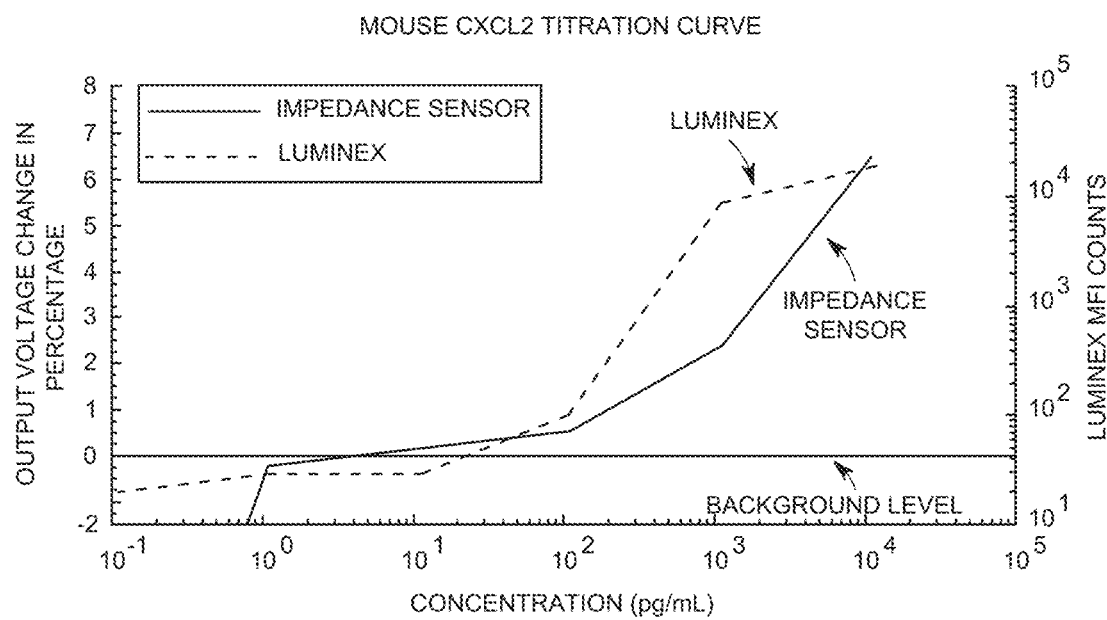

FIG. 25 illustrates nonspecific binding data, here rat serum, superimposed with a power fit and a linear fit.

FIGS. 26A-26D illustrate mouse cytokine titration curves in spiked serum and comparison of impedance sensor data with Luminex data.

Figures 27A, 27B:
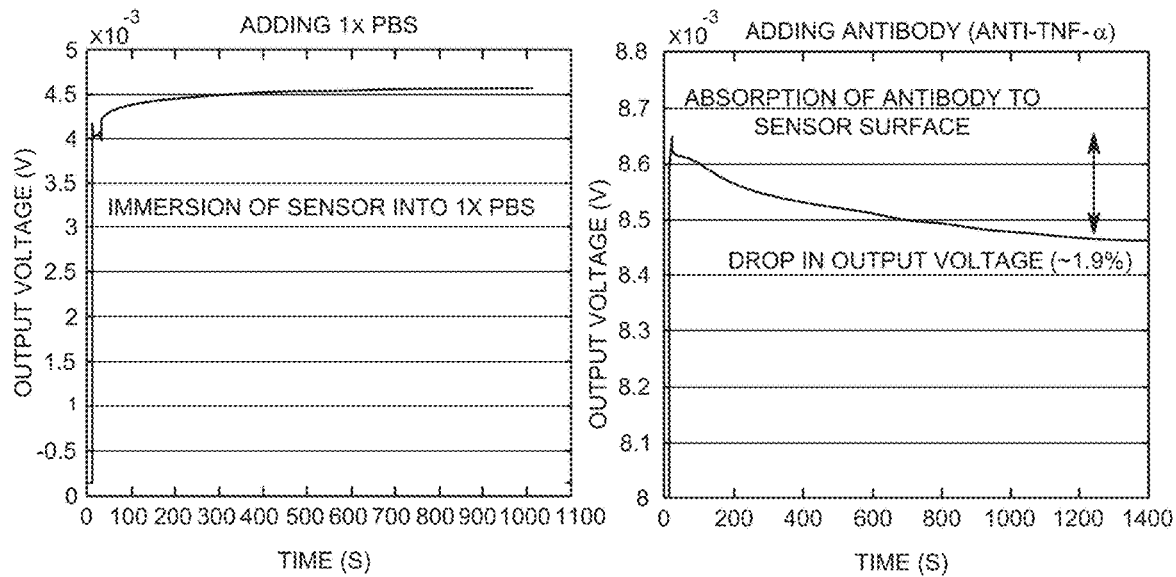
Figure 27C:
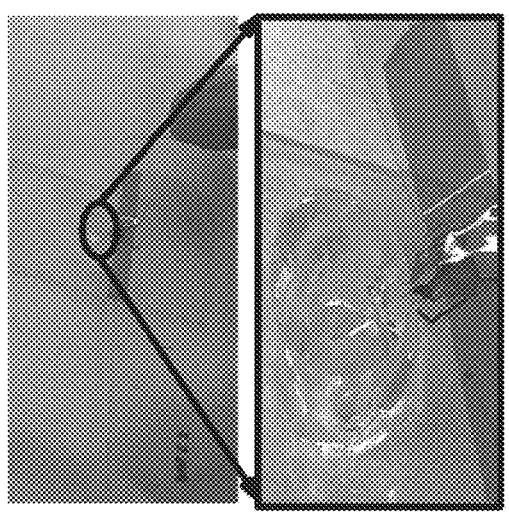
Figure 27D:
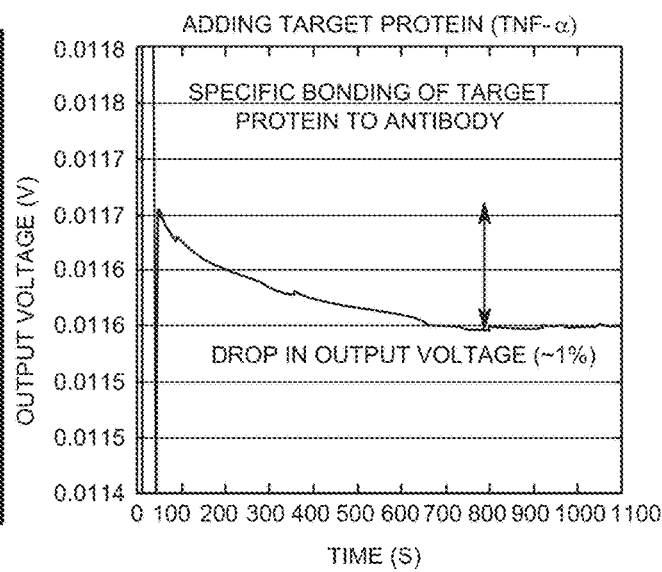

FIGS. 27A-27D illustrate needle-sensor functionality post insertion. FIGS. 27A, 27B, and 27D show lock-in amplification data at 1 MHz. FIG. 27C illustrates a sensor on glass needle that is inserted through a vertical skin phantom after antibody immobilization.

Figure 28A:
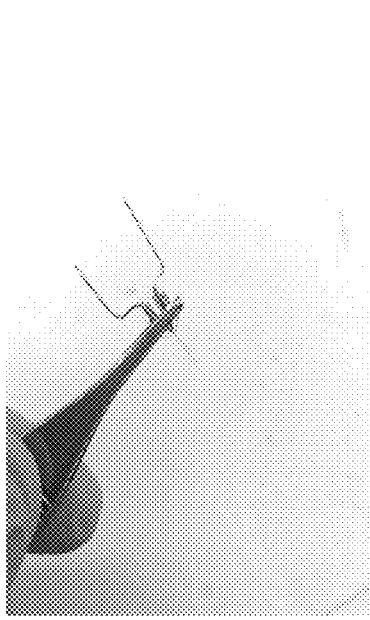
Figure 28B:
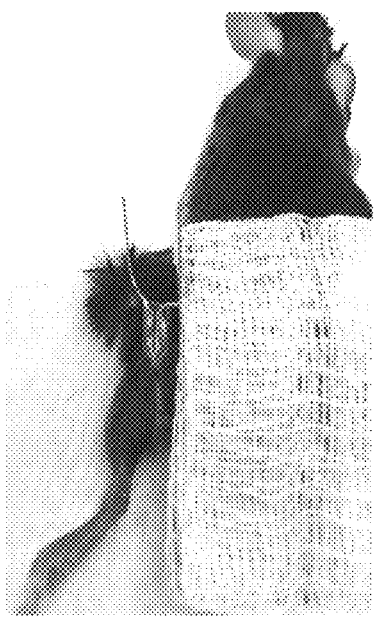
Figure 28C:

FIG. 28A illustrates manual insertion of a sensor by holding the sensor connector with tweezers. The sensor is inserted in the left rear limb muscle of a mouse by piercing through intact skin. FIG. 28B shows the sensor facing front and FIG. 28C shows the sensor facing back.

Figure 29:
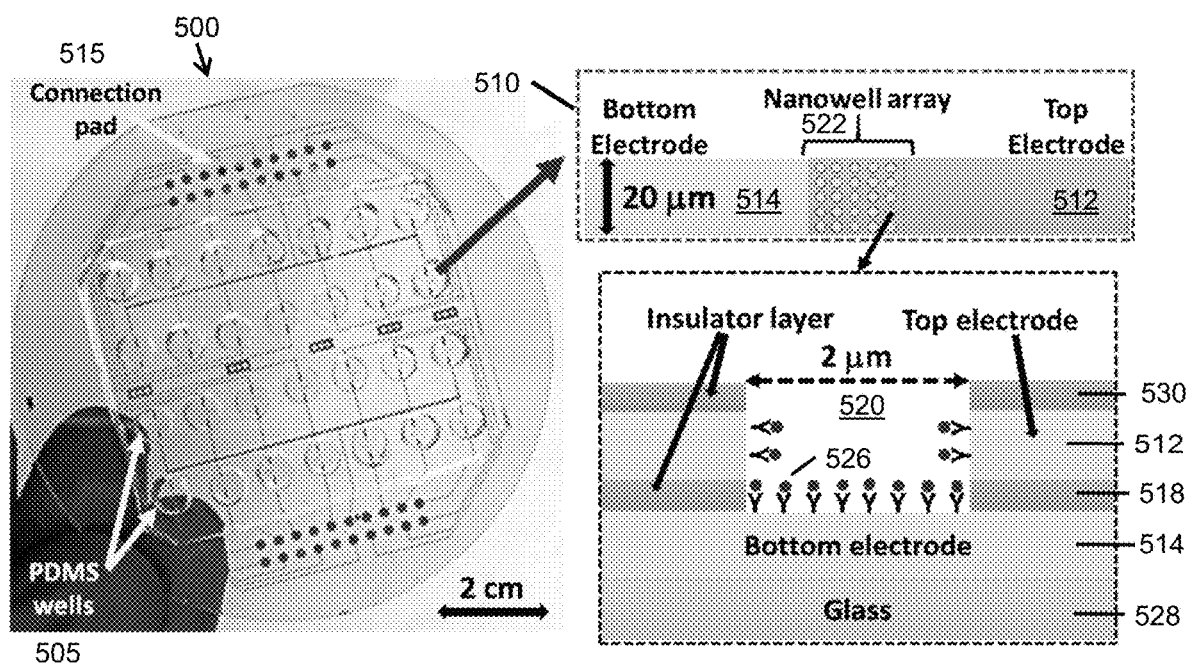

FIG. 29 illustrates a multi-well plate chip and schematic views of a 2-μm array sensor and a single nanowell. The sensor comprises an array of 25 nanowells etched on the overlapping electrode surface.

DETAILED DESCRIPTION

A description of example embodiments follows.

Embodiments of this invention relate to novel biosensors for minimally invasive, transcutaneous, and continuous monitoring of cytokines in circulating blood. Diagnostic and monitoring biosensors are useful for disease diagnosis. The biosensors described herein are label-free, can tolerate high salt condition in blood, and are highly sensitive, e.g., can detect an analyte(s) at low concentrations, such as in the femtoMolar (fM) range.

Described is a flexible micromachined needle-shaped impedance sensor for label-free, real time, in-situ detection of cytokines and other biomarkers in circulating blood. The sensor utilizes a micro-well array configuration at the needle tip to enable label-free detection while being capable of high-sensitivity detection despite high salt concentration of the complex biological matrix.

In an embodiment, the sensor includes a 100 μm×100 μm micro-well array comprising 289 individual wells and is configured on the tip of a flexible micromachined needle. Antibodies (or aptamers) are immobilized inside the wells. Binding of target antigen modulates the impedance between the electrodes, resulting in a rise of impedance due to partial occlusion of ions passing between the two electrodes inside the micro-well (nanowell).

Figure 12:
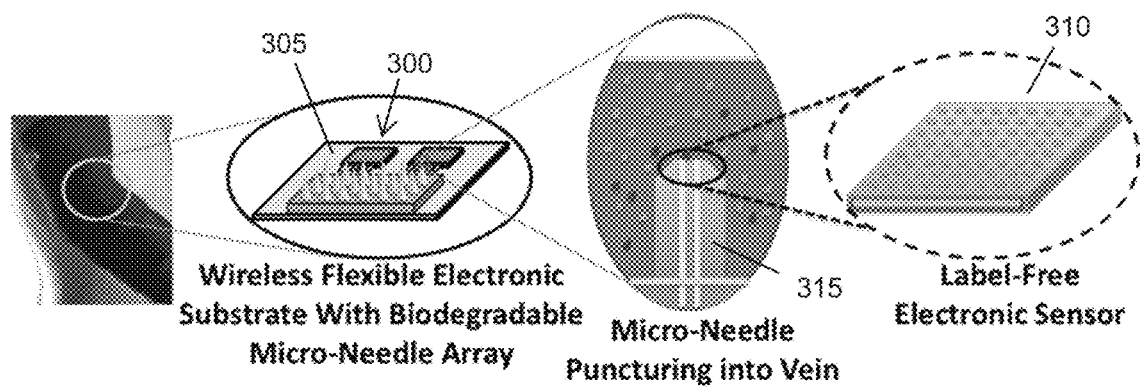
FIG. 12 illustrates a smart bandage including a 2-D array of micro-needles on a flexible substrate with label-free fabricated on top of needles (one sensor per needle tip).
Figure 13:
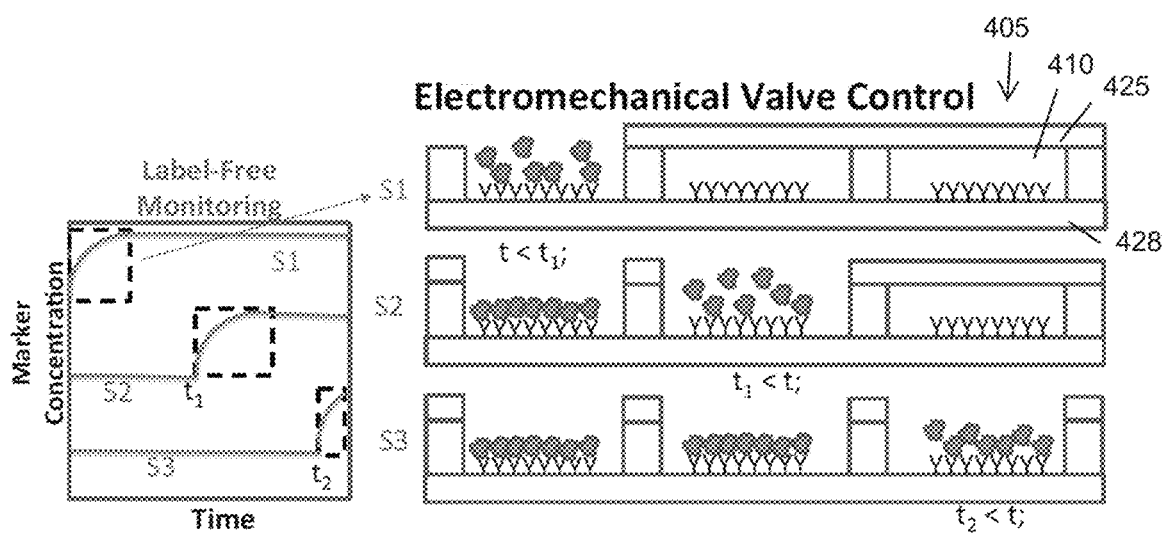
FIG. 13 illustrates a label-free electronic biomarker sensor including a 2-D array of nano-pores (wells) functionalized with antibodies for monitoring protein binding to the sensor surface. The sensors of the array are veiled by a thin conductive membrane and can be unveiled sequentially, thereby enabling continuous monitoring.

Embodiments of this invention further relate to a method for minimally invasive and continuous label-free quantification (and monitoring) of biomarkers including cytokines and other proteins/peptides in serum within minutes at fM concentrations. Embodiments can be adapted for and/or incorporated in a transcutaneous patch sensor based on the flexible micromachined needle-shaped impedance sensor. Additional embodiments of a smart bandage or patch are described below and are illustrated in FIGS. 12-13.

Embodiments can be used with or incorporated in a wearable biosensing platform. A purpose of the biosensing platform can be to continuously monitor biomarkers of inflammation in the bloodstream in response to stimulation of the peripheral nervous system for treatment of chronic inflammatory diseases.

Inflammatory cytokines can rise as a result of chronic inflammatory disease without the involvement of nervous system. Thus, another purpose of the biosensing platform can be to continuously monitor biomarkers of inflammation in the bloodstream for treatment of chronic inflammatory diseases.

An impedance biosensor for electrical impedance biological sensing and manufacturing method thereof are described in U.S. patent application Ser. No. 13/837,451, filed Mar. 15, 2013, and published May 29, 2014 as US2014/0147336A1, the relevant teachings of which are incorporated herein by reference.

A biosensor device to detect target analytes in situ, in vivo, and/or in real time, and methods of making and using the same are described in International Application PCT/US2016/055706, filed Oct. 6, 2016, and published Apr. 13, 2017 as WO2017/062591A1, the relevant teachings of which are incorporated herein by reference.

Example 1

Nanowell Array Impedance Sensor for Label-Free Quantification of Cytokines in Serum at Femtomolar Level Detection Limits Presented herein is a novel method for label-free quantification of cytokines in serum within ten minutes at femto-Molar concentrations. Detection of proteins in blood using label-free impedance based techniques is difficult due to high salt concentration of the matrix, which results in screening of the charge of the target proteins. A novel sensing configuration is described where sensitivity benefits from the high salt concentration of the matrix, and robust performance is demonstrated through testing in rat serum.

FIG. 1 shows a schematic illustration of the basic sensor device 10. It includes a pair of conducting electrodes 12, 14 that are separated by a nanometer-sized (e.g., 50 nm) gap 16. The electrodes can be gold electrodes. An array 22 of micro-wells (e.g., pores) 20 is formed on the sensor surface and extending through the upper electrode 12 and an insulator 18 positioned between the upper electrode 12 and the lower 14 electrode. Antibodies 24 are immobilized inside the wells 20. Binding of target antigen 26 modulates the impedance between the electrodes, resulting in a rise in impedance due to partial occlusion of ions passing between the two electrodes 12, 14 inside the well. Higher salt concentration results in larger current, thus higher signal power corresponding to larger changes in current due to protein binding. The electrodes 12, 14 and the insulator 18 are fabricated on a substrate 28. The upper electrode 12, which defines the wells 20, is covered with a protective layer 30. The sensor can further include circuitry 32 coupled to the electrodes, the circuitry applying the electrical voltage to the sample in the wells via the electrodes and measuring a current via the electrodes in response to the voltage applied. The modulated impedance between the electrodes can be determined as a function of the voltage applied and the current measured. The circuitry 32 can include a lock-in amplifier.

FIGS. 2A-2B show microscopic images of microfabricated sensors. The sensor was fabricated using gold electrodes on a glass substrate. Bonding pads are fabricated on opposing sides of the micro-chip with traces leading to the center of the chip. The two electrodes overlap with each other and are separated by a thin (e.g., 40 nm, 50 nm, generally 40 nm-50 nm) aluminum oxide layer. The top electrode is also covered with a protective oxide layer. In the overlapping region of the two electrodes, the top electrode and the insulator of the sensor are micro-patterned with holes that expose the bottom electrode to solution. A lock-in-amplifier is used to monitor the impedance across the electrodes continuously in real-time. The lock-in amplifier and any other circuitry can be coupled to the electrodes via the bonding pads.

Figure 3A:
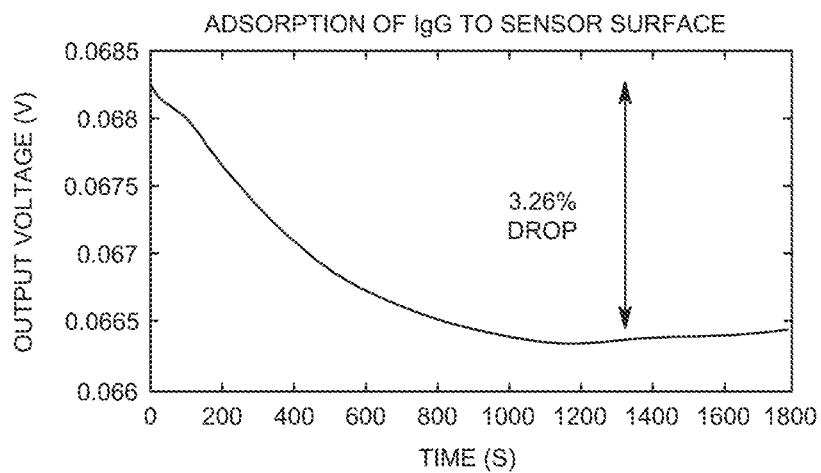
FIGS. 3A-3C show plots of output voltage as a function of time obtained with an example embodiment of the impedance sensor.
Figure 3B:
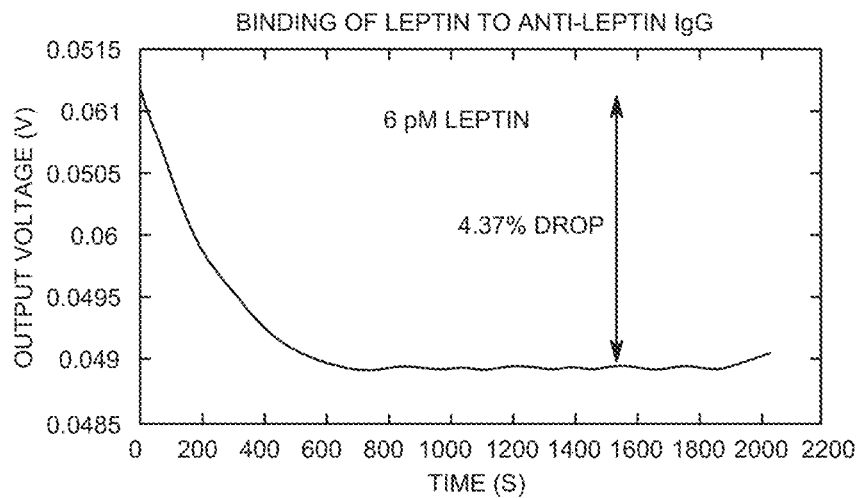
Figure 3C:
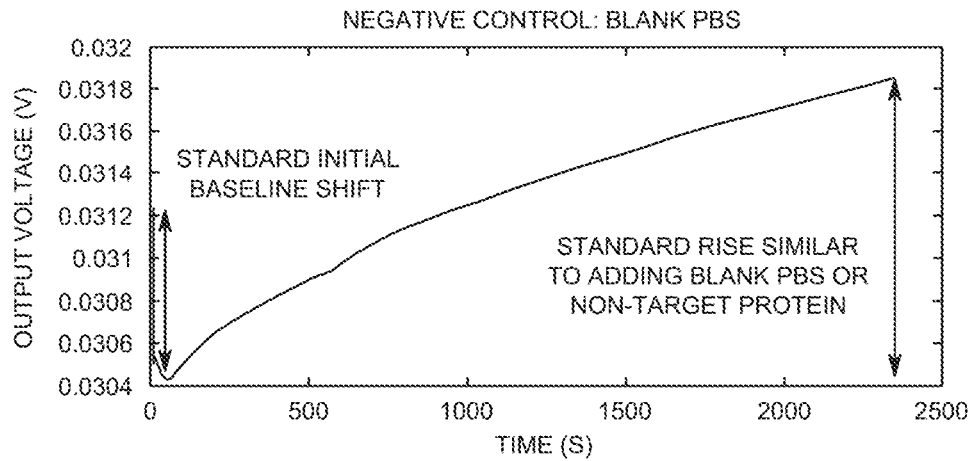

The ability of the sensor to detect target cytokine in both Phosphate Buffer Saline (PBS) and rat serum at low concentrations was repeatedly tested. FIG. 3A shows representative data of physical adsorption of the probe antibody (anti-leptin IgG) for functionalization of the base electrode. FIG. 3B shows representative data of binding of leptin to anti-leptin IgG, and FIG. 3C shows data from various negative control experiments. Saturation occurs in less than 10 minutes. Testing demonstrated detection of leptin in purified buffer at concentrations as low as 60 fM.

Figure 4A:
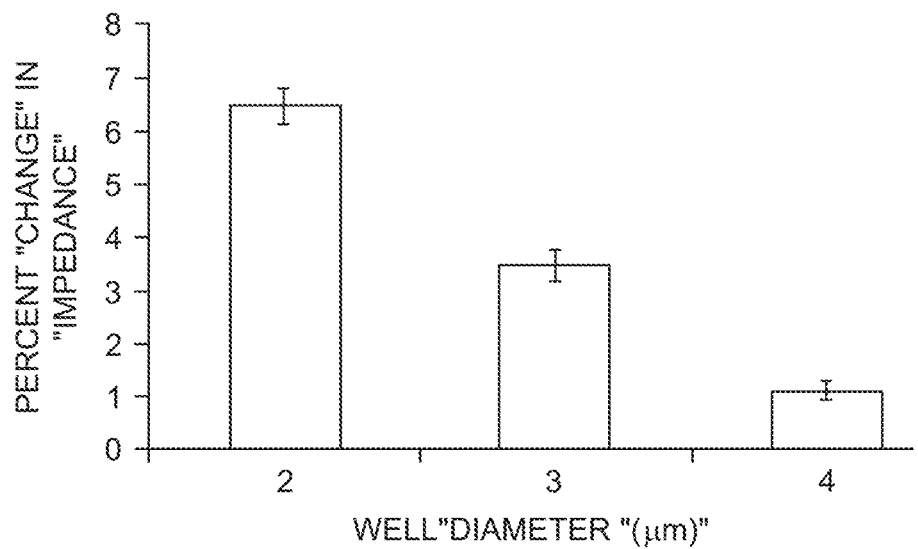
FIG. 4A illustrates the relationship between sensitivity and well diameter measured in triplicate over 3 different well sizes.
Figure 4B:
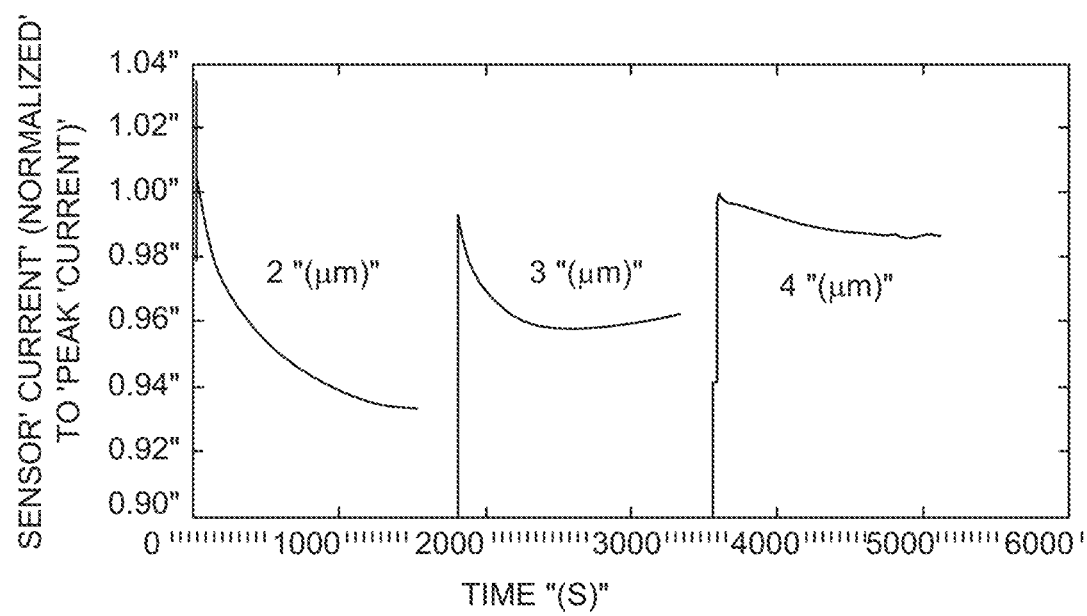
FIG. 4B illustrates current across the electrodes versus time for 2 μm, 3 μm, and 4 μm diameter wells.

Also tested was the role that sensor diameter plays in sensitivity of the device. FIGS. 4A-4B show the effect of changing the well diameter on the response of IgG physically adsorbing to the sensor surface. Smaller sensor diameter, e.g. 2 results in improved sensitivity, as illustrated in FIG. 4A, which is due to the fact that the change in resistance (impedance) becomes larger with respect to the sensor baseline resistance.

Figure 5:
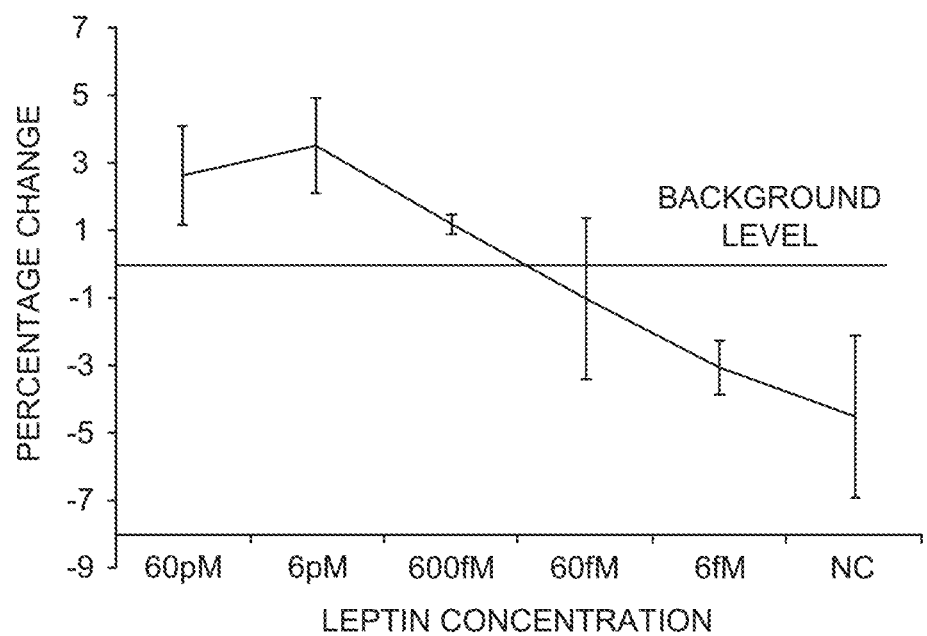
FIG. 5 illustrates a titration curve for analyte concentrations (here, Leptin concentration) ranging from 60 picoMolar (pM) down to 6 femtoMolar (fM). Error bars are standard deviation over 3 points. Negative control (NC) is also included. Background level is defined where change in impedance across electrodes is no longer positive. 600 fM is clearly above background.

FIG. 5 shows a titration curve for testing 2 μm diameter nanowell sensors, where a broad range of concentrations has been tested in rat serum. Reliable detection of leptin is shown at 600 fM and higher. All experiments were performed by spiking leptin into rat serum, and performed in triplicate. All negative control measurements were performed using non-spiked rat serum to ensure that sensor fouling did not result in false-positive signals.

Example 2

Microwell-Array on a Flexible Needle: A Transcutaneous Insertable Impedance Sensor for Label-Free Cytokine Detection Described herein is a flexible micromachined needle-shaped impedance sensor for label-free in-situ detection of cytokines and other biomarkers in the blood stream. The sensor utilizes a micro-well array configuration at the needle tip to enable label-free detection while being capable of high-sensitivity detection despite high salt concentration of complex biological matrix, as described in EXAMPLE 1 above and in the article by P. Xie, N. Song, W. Shen, M. Allen and M. Javanmard, MicroTAS 2017. The sensor, which includes a 100 μm×100 μm micro-well array comprising 289 individual wells, is placed on the tip of a flexible micromachined needle. To mimic in-vivo measurements, the sensor-bearing microneedle has been inserted into a skin phantom using a temporary, stiff backing that is completely removable after insertion of the sensor, to minimize mechanical damage to tissues. Real-time label-free detection is achieved in the phantom via monitoring the impedance change across the sensor electrodes as binding of target protein to the antibody occurs.

The ability to measure proteins in bodily fluids can enable continuous health monitoring. The gold-standard technique for protein quantification is ELISA, which typically relies on optical fluorescence, and labeling of complementary antibody, resulting in lengthier and more costly testing. Impedance sensors provide a promising alternative due to ease of miniaturization and label-free operation, yet lag behind their fluorescent counterparts in terms of sensitivity (see, e.g., J. S. Daniels, and N. Pourmand, Electroanalysis, 2007 May 16, pp. 1239-1257). Nano-well impedance sensors on glass substrates have capabilities of femtomolar level detection of cytokines, as described in Example 1 (see also P. Xie, N. Song, W. Shen, M. Allen and M. Javanmard, MicroTAS 2017). However, these stiff sensors do not have an insertion form factor and may have limited chronic application in vivo due to the large sensor/tissue mechanical mismatch (see, e.g., W. Shen, L. Karumbaiah, X. Liu, T. Saxena, S. Chen, R. Patkat, R. Bellamkonda and M. G. Allen, Microsystems & Nanoengineering 2015). The label-free impedance sensor described here is flexible yet can be inserted into tissue directly.

Figure 6:
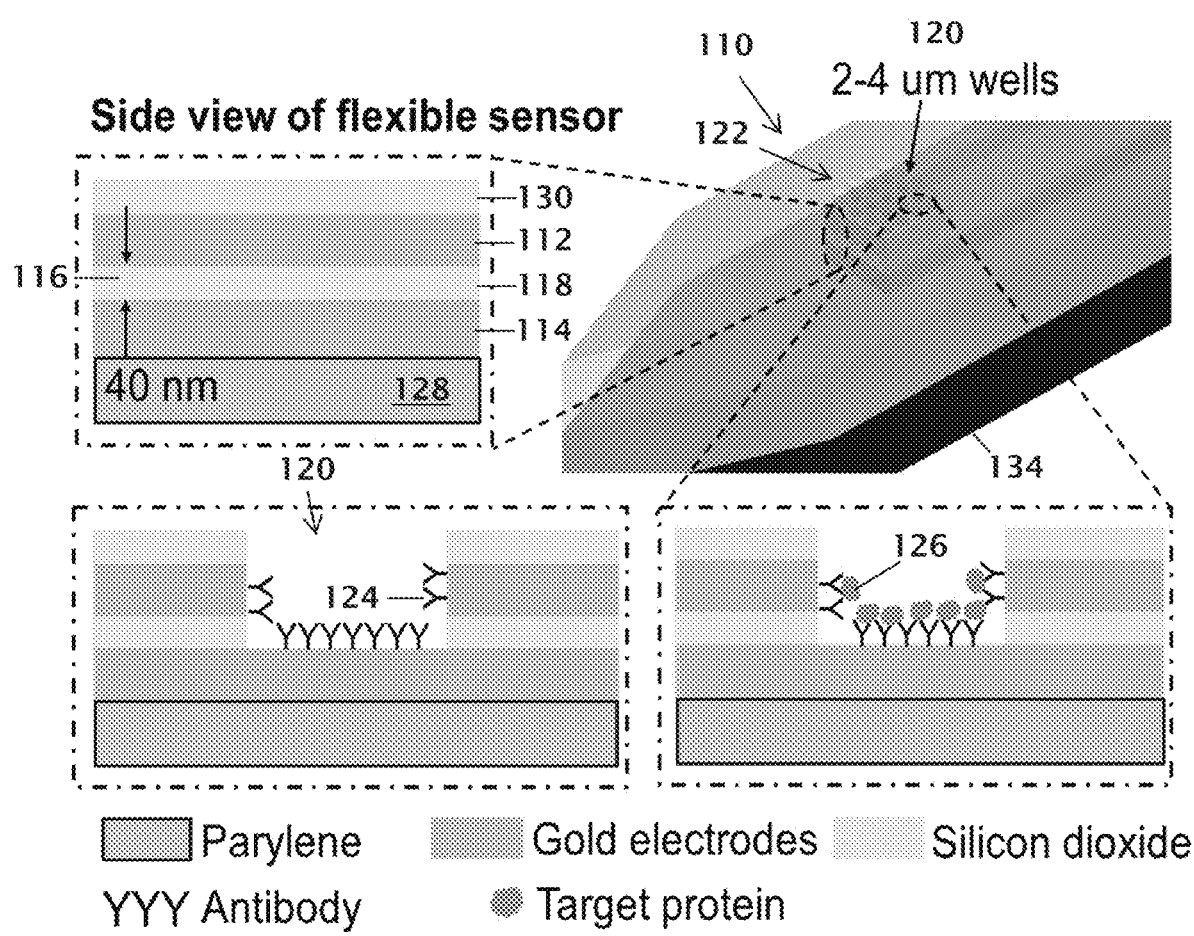
FIG. 6 is a schematic illustration of a label-free flexible sensor according to an example embodiment of the invention. The sensor is shown on a tip of a needle-shaped insertion device. Specific binding of target protein to the antibody, which is immobilized on sensor surface, results in an increment in impedance across electrodes.

FIG. 6 shows a schematic of the flexible sensor 110, comprising a pair of gold electrodes 112, 114, separated by a 40 nm insulation layer 118 of silicon dioxide. Similar to sensor 10 (FIG. 1), the sensor device 110 includes a pair of conducting electrodes 112, 114 that are separated by a nanometer-sized (e.g., 40 nm) gap 116. As shown, the electrodes can be gold electrodes. An array 122 of micro-wells (e.g., pores) 120 is formed on the sensor surface and extending through the upper electrode 112 and an insulator 118 positioned between the upper 112 and lower 114 electrodes. Antibodies 124 are immobilized inside the wells 120. Binding of target antigen 126 modulates the impedance between the electrodes, resulting in a rise in impedance due to partial occlusion of ions passing between the two electrodes 112 and 114 inside the well 120. Higher salt concentration results in larger current, thus higher signal power corresponding to larger changes in current due to protein binding. The electrodes 112, 114 and the insulator 118 are fabricated on a substrate 128. The upper electrode 112, which defines the wells 120, is covered with a protective layer 130. The sensor can further include circuitry (see 32, FIG. 1) coupled to the electrodes 112, 114. The circuitry is configured to apply an electrical voltage to the sample in the wells via the electrodes and measure a current via the electrodes in response to the voltage applied. The modulated impedance between the electrodes can be determined as a function of the voltage applied and the current measured.

The fabrication process is schematically detailed in FIGS. 7A-7F. A fused silica wafer 127 is coated with a layer of parylene 128 (FIG. 7A). Two gold electrodes 112, 114 and bonding pads are lithographically defined (FIG. 7B). Insulation layers of silicon dioxide between 118 and on top 130 of the gold are deposited using atomic layer deposition. The microwells 120 in the overlapping region of the two electrodes are patterned using sequential reactive ion etching of SiO2 and wet etching of gold (FIG. 7C). The flexible sensor 110 is laser micromachined into its needle shape and released from the silica substrate 127 (FIG. 7D). To assist the insertion process, the sensor 110 is integrated with a laser micromachined stainless steel insertion device 134 (FIGS. 7E-7F), which is withdrawn post-insertion. FIG. 7F is a 3D view of the sensor 110, including the needle-shaped tip 111 and the wider section having the contact pads (i.e., bonding pads) 136 for coupling the sensor electrodes to circuitry for impedance measurements.

FIGS. 8A-8B show a fabricated, functional flexible sensor 110. After the sensor is fabricated, the probe antibody, tumor necrosis factor alpha (TNF-α), is immobilized on the sensor surface inside the wells. After the insertion of the flexible sensor through the skin phantom into the fluidic cell, specific binding of target protein to the antibody results in an increment of impedance across the two electrodes due to the reduction of ion transfer in the solution. As a result, real-time detection of the target protein can be achieved via continuously monitoring the impedance.

Experimental Results

Figure 9A:
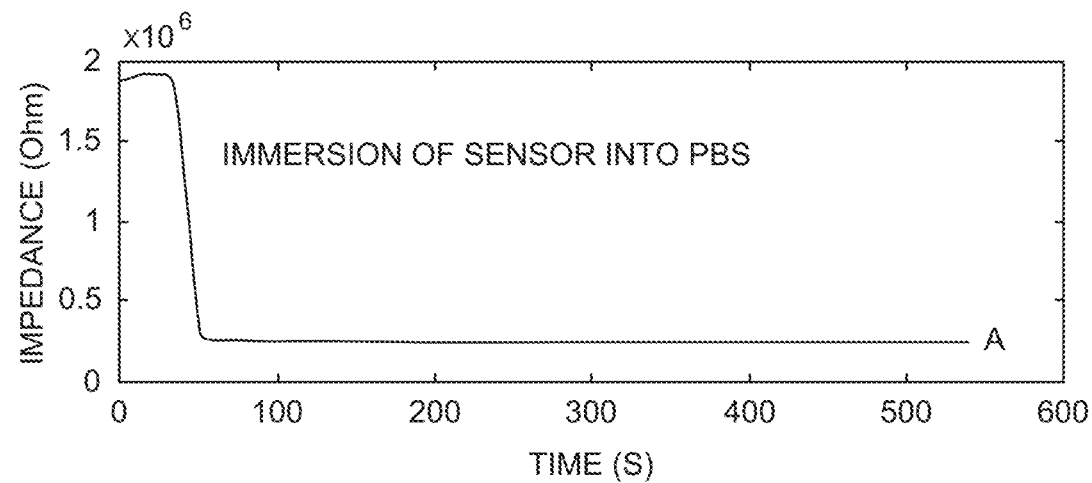
FIGS. 9A and 9B illustrate impedance across electrodes at 1 M Hz measured by potentiostat with different sensor environments.
Figure 9B:
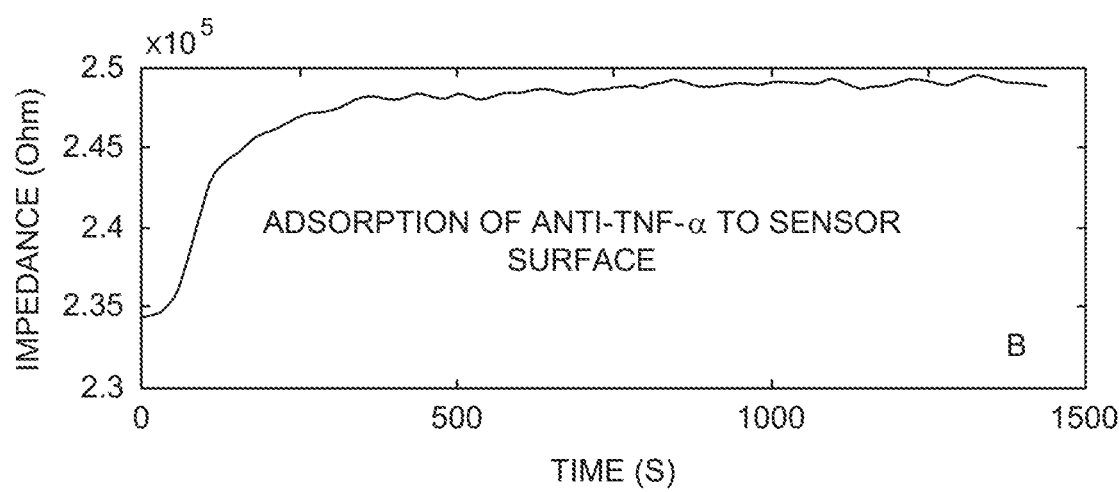

Electro-chemical impedance spectroscopy (EIS) and real-time lock-in-amplification measurements are used for data recording and analysis. FIG. 9A shows the impedance change across the electrodes after immersion into Phosphate Buffered Saline (PBS) and FIG. 9B the physical absorption of the probe antibody (anti-TNF-α) before insertion.

Figures 10A, 10B, 10C, 10D:
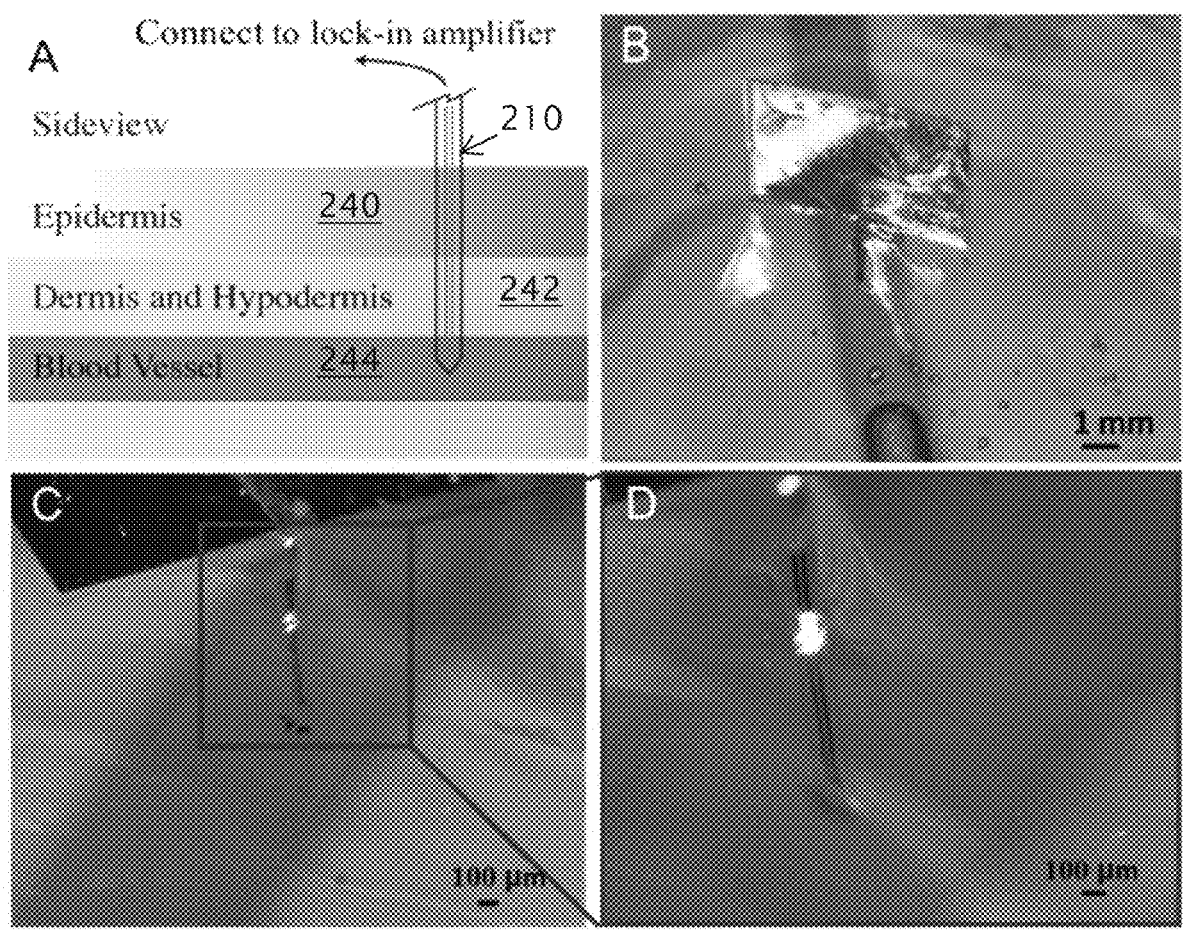
FIGS. 10A-10D illustrate deployment of a sensor into a skin phantom according to an example embodiment of the invention.

FIGS. 10A-10D illustrate insertion of the flexible sensor 210 through a skin phantom into a fluidic channel. The phantom is constructed (FIG. 10A) to emulate the skin tissues (epidermis 240, dermis and hypodermis 242) and the blood vessel 244. Removal of the stiff backing, (see, e.g., insertion device 134 of FIG. 7F) as shown in FIGS. 10C-10D, results in similar mechanical properties of the sensor and the phantom, which may be useful for in vivo applications.

Figure 11A:
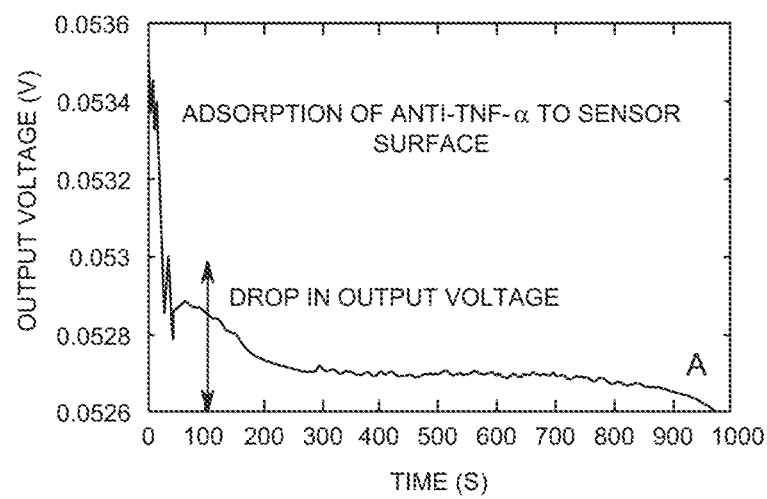
FIGS. 11A-11C illustrate example data of lock-in amplification at 1M Hz.
Figure 11B:
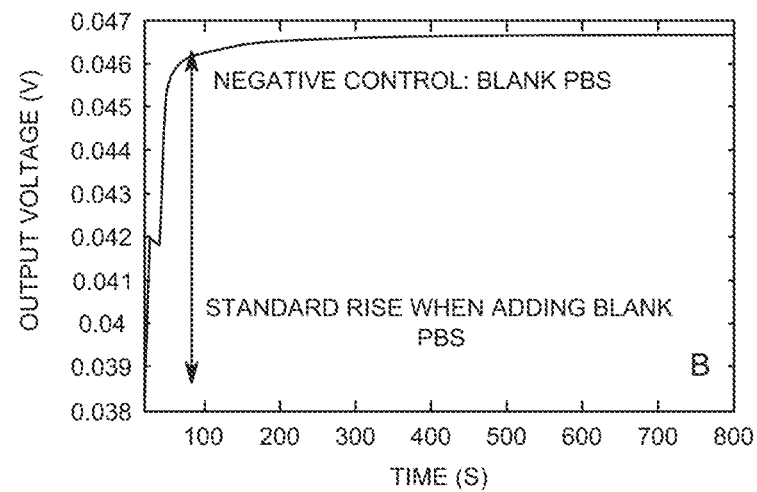
Figure 11C:
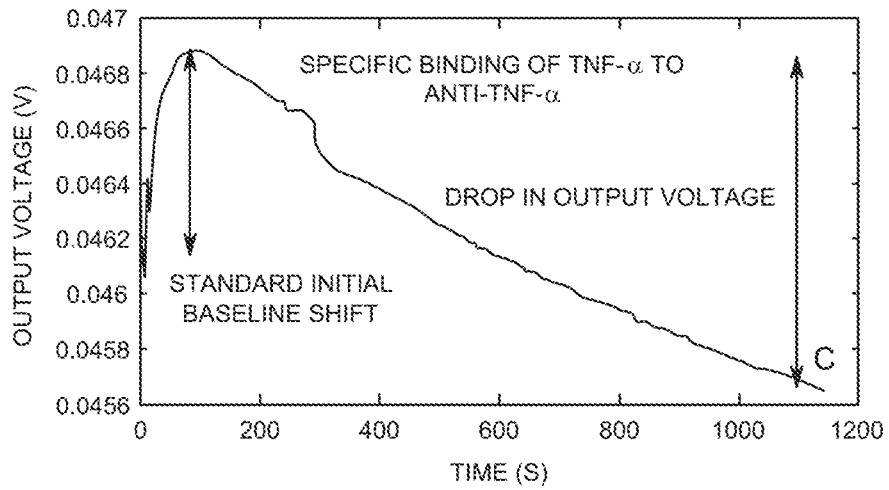

FIGS. 11A-11C show a set of representative experimental results of the immobilization of probe antibody on the sensor surface, specific binding of TNF-α to anti-TNF-α, as well as negative control steps after the insertion of the flexible sensor through the skin phantom. Testing of the sensor has demonstrated the capability of the flexible sensor to detect TNF-α in 1×PBS at a concentration of 1 nM after insertion.

Example 3

Smart-Patch

In some embodiments, aspects of the invention relate to an in-vivo battery-powered electronic sensing and actuation platform for continuous monitoring of key human signaling molecules with high temporal density (>1 measurement per 5 minutes) over long periods of time (>24 hours): the ProteOhmic Smart-Patch. This continuous physiological monitoring approach works by detecting protein biomarkers and metabolites in label-free multiplexed format using a "ProteOhmic" sensor, that includes an array of needles made of natural substrates, each with graphene sensors mounted on the tip.

FIG. 12 illustrates a smart bandage 300 including a 2-D array 305 of micro-needles 315 on a flexible substrate with label-free sensors 310 fabricated on top of needles (one sensor per needle tip).

Continuous monitoring of biomarkers using the ProteOhmic Smart-Patch has a multitude of applications that can impact the military including monitoring of key signaling pathways (e.g. inflammation) during wound healing, bed sores, and even biomarker monitoring for human performance enhancement during training and combat. For example, a generalizable miniaturized transcutaneous interface can be used for quantifying biomarkers continuously in response to neural stimulation, both with high temporal density to capture the transient response of the effects of neural stimulation in circulating markers, along with the long term physiological responses as well.

FIG. 13 illustrates a label-free electronic biomarker sensor including a 2-D array of nano-pores (wells) functionalized with antibodies for monitoring protein binding to the sensor surface. An array 405 of sensors 410 is fabricated where all sensors are veiled by a thin conductive membrane 425. Sensors are unveiled sequentially (S1, S2, S3) enabling continuous monitoring. Each label-free sensor can be fabricated on a natural substrate 428.

Embodiments of the invention relate to a platform technology generalizable to a wide array of biomarkers. This can involve the use of ultra-compact sensors with sensitivity high enough to assay low abundance markers, yet resilient against corrosion and fowling, and a functionalized sensing surface, which is reusable. The Smart-Patch will benefit from recent innovations in label-free sensing, actuation, flexible electronics, BioMEMS substrates with minimal inflammatory response, and nanofluidic sample preparation and delivery techniques to form a unique fully integrated wearable solution for continuous transcutaneous monitoring of key inflammatory markers in blood without the need for repeated venipuncture. In some embodiments, the platform is implemented as a wearable micro-chip.

Key transformational elements of some embodiments of the invention can include one or a combination of the following: 1) The ability to continuously monitor and rapidly track changes occurring in protein biomarker concentrations (>1 sample per 5 minutes) over periods of time greater than 24 hours at a sensitivity of 10 fM; 2) formation of an array of innovative label-free biosensors on a battery powered flexible substrate for continuous biomarker level monitoring; and 3) high aspect ratio minimally invasive needles which can puncture through the skin to access blood directly (FIG. 12). As an example of the functionality of the Smart-Patch, it can monitor the targeted proteins in real time, and transmit the information wirelessly to an ex-vivo processing unit, which would provide real-time feedback to the ProteOhmic Sensor chip.

The generalizable interface can be applicable to a wide array of chronic and acute conditions. One application is to apply the platform technology to monitoring inflammatory markers involved in rheumatoid arthritis (RA). RA results from an imbalance in pro-inflammatory and anti-inflammatory cytokine levels. In RA, cytokines such as TNFα and IL1 promote inflammatory responses and consequently destruction of the joints. Anti-inflammatory cytokines such as IL4, IL10, and IL13 are present systemically as well as locally in rheumatoid joints, but their levels are insufficient to neutralize inflammatory response caused by pro-inflammatory cytokines.

In some embodiments, the invention relates to in-vivo continuous monitoring of inflammatory marker levels in response to neuro-stimulation.

Label-Free Sensor

In some embodiments, at the heart of the Smart-Patch 300 is a battery powered micron-scale chip impregnated with an array 305 of micro-needles 315 (FIG. 12), where the tip of each needle has a label-free biosensor 310 mounted on top.

Leveraging previous experience in designing impedance based biosensors, a new class of sensors can be used by forming graphene based electrodes separated by a thin porous oxide layer functionalized with antibodies against the target molecule of interest. The small electron transfer resistance (yet no corrosion) of graphene electrodes makes them suitable for high sensitivity and low-power impedance measurements through the porous material (see, e.g., FIGS. 1, 12, and 13), while being resistant to fowling. Voltage can be applied and the increase in impedance between the electrodes serves to monitor protein binding in real-time. The architecture allows for the formation of multiple sensors on a single chip, each functionalized with a different antibody to enable multiplexed detection in an ultra-compact structure. Various passivation techniques, such as use of polyvinylphosphonic acid (PVPA) chemistry, have been demonstrated as a viable technique for allowing immobilization of enzymes and proteins inside pores.

Analyte Diffusion into Wells

One of the limits faced by nanopores is the slow rate of diffusion of analyte inside the wells, thus requiring nano-Molars of analyte concentration. Since each of the micro-needle sensors consists (in some embodiments) of large numbers (e.g., thousands) of nanopores (wells), transport and thus translocation into the pore will be enhanced by several orders of magnitude compared to a single pore.

In some embodiments, the invention relates to a wearable device that can repeatedly measure (sampling rate: from 1 measurement/min to 1 measurement/5 min) the concentration of biological samples over long periods of time (lifetime range from 24 hours to 6 months), something that is unachievable with gold standard techniques like ELISA and even with emerging labeled and label-free technologies that have been presented in the literature over the years.

In some embodiments, the invention relates to the ability to continuously monitor health at the molecular level at high temporal resolution over long periods of time; and in some embodiments, provides at least 100× improved sensitivity compared to ELISA and 10× decrease in analysis time.

Advantages and Features

Aspects of the invention relate to devices and methods involving sensors that overcome one, any combination, or preferably, all, of the key limitations of prior approaches, namely:

1) Since the present approach is based on measuring the resistance between the two graphene electrodes, higher conductivity buffer (like blood) will result in higher currents, and thus larger electronic signal to noise ratio resulting from analyte binding to the sensor active area (see Emaminejad, S.; Javanmard, M.; Dutton, R. W.; Davis, R. W., Microfluidic diagnostic tool for the developing world: Contactless impedance flow cytometry. *Lab on a Chip* 2012, 12 (21), 4499-4507).
2) The electronic Signal-to-Noise Ratio resulting from antigen binding in the sensor improves as the graphene electrode area increases (keeping distance between the two graphene layers fixed), because increase in sensor width results in higher currents and thus larger SNR. This phenomenon was previously demonstrated on the microscale in the context of cytometry and the same improvement will translate to nanoscale.
3) Larger nanopore radii result in improved analyte acquisition time and detection limit (see Table 1 below). The flexibility to use larger sensor surface area and larger pores can result in higher repeatability to due smaller assay-to-assay variations.
4) Last but not least, improvement in accuracy can be gained using an array as opposed to a single measurement. By fabricating hundreds, even thousands of needles on the flexible substrate, one can achieve significant redundancy, and can dynamically perform self-calibration and cross-correlation measurements between sensors operating in parallel. Sensors operating out-of-range can be turned off similar to faulty segments in memory being shut down without the awareness of the end-user.

In short, in some embodiments, the disclosed technique boasts the advantages of micro-scale sensors in achieving higher analyte capture efficiency along with improved reproducibility, while achieving the single-molecule electronic detection levels associated with nanoregime devices.

Non-Specific Binding

In some embodiments, the technology in assaying human serum for 116 with a background of leptin at 1000× higher concentration, and showed minimal non-specific binding. Similarly, an assay targeting leptin in human serum with a background of 116 at 1000× higher concentration also showed minimal non-specific binding. Blocking of the surface was performed using Bovine Serum Albumin. In some embodiments, the specificity can be at least as good as ELISA. Non-specific binding can be managed with high-quality antibodies, optimum blocking buffer, and a passive PEG hydrogel layer at the sensor surface. In some specific embodiments, non-specific binding is kept at levels lower than a detection limit of the assay and/or lower than about 10 fM.

Real-Time Detection/Frequency of Measurements

Real-time detection refers to the ability to continuously perform measurements with a temporal-density of at least the fastest biological event being measured for the necessary duration.

Example 4

In some embodiments, the invention relates to performing measurements at a minimum sampling rate of one sample per five minutes, which is more than adequate for monitoring changes in most common chronic diseases, such as rheumatoid arthritis where changes in molecular levels occur over hours and even days.

Sampling rates on the order of seconds can be suitable for monitoring acute conditions as well (Table 1). The required sampling rate varies depending on the disease of interest, particularly depending on whether the condition is acute or chronic. According to the literature, protein biomarkers involved in chronic diseases have cycles on the order of hours and even days, however it is possible that higher temporal density can provide more information. In the case of acute conditions, such as trauma or cardiac injury, the cycles can be much faster, potentially down to minutes and even seconds.

The fastest sampling can depend on the analyte acquisition time, which depends on the diffusion rate and binding kinetics of the target antigen with the probe antibodies and how fast the measurement can be acquired. This depends on 1) electrical sensitivity, 2) antibody affinities, and the 3) geometrical dimensions of the sensor. Table 1 presents modeling results of the effect that the nanowell (pore) diameter has on the signal-to-noise ratio (SNR) (resulting from antigens getting captured in the wells), and the time which it takes for sufficient analyte to accumulate on the sensor surface to get accurately measured.

From past work (Emaminejad, S.; Javanmard, M.; Dutton, R. W.; Davis, R. W., Microfluidic diagnostic tool for the developing world: Contactless impedance flow cytometry. *Lab on a Chip* 2012, 12 (21), 4499-4507) a comprehensive noise model for predicting the signal-to-noise ratio of resistive pulse based sensors applicable to both micro- and nano-electrode systems was developed. As shown in Table 1, smaller nanopore diameter results in higher electronic signal-to-noise ratio for single antigen binding. One reason is because smaller pore size results in smaller pitch size allowing for a higher density array of pores per sensor. Also, with smaller pores, the ratio ($\Delta R/R$) of change in resistance with respect to the resistance across the pore increases. By combining the noise model with first-order Langmuir equations, one can calculate analyte capture and detection time. Analyte acquisition time is significantly slower for 20 nm pores compared to larger sized pores (300 nm). It is predicted that the 300 nm pores will have very rapid acquisition times (<1 s). The reason for this is because, larger pore diameters have larger numbers of immobilized capture antibodies which makes it is easier for target antigens to get captured in the pores. Thus, while electronic SNR is lower for larger pores, analyte capture rate greatly increases as pore size increases, thus allowing for faster analyte sampling rate.

Based on previous experience with fabricating label-free sensors, and the analytical modeling (Table 1), the sensing structure can have very high sensitivity, and thus is expected to accurately detect changes in cytokine concentration very rapidly (within one minute).

Example 5

Sensor Calibration

Dynamic sensor calibration can allow for highly accurate and repeatable quantification of analyte. Real-time calibration of the sensors can be performed through performing multiple measurements simultaneously with diversity. Here, differential measurements can be made with respect to sensors with passive surfaces where minimal adsorption is expected, and also with respect to sensors with titrated quantities of antibody patterned on the sensor surface. This can provide a calibration curve with a dynamic range allowing one to accurately quantify antigen levels. This latter approach is similar to antigen titration based calibration currently done with commercially available ELISA kits. The advantage of having an array of needles for performing a multitude of measurements is that cross-correlation measurements can dynamically be performed during data acquisition to ensure sensors are operating accurately. When a sensor falls outside the operational range, the needle can be turned off similar to when a memory segment becomes faulty in a hard drive.

Example 6

Multiplexing Capabilities

In some embodiments, in principle, each patch can analyze 100 analytes, where each needle in the array will have a different antibody immobilized on the tip.

In some embodiments, using standard protein arraying technology, 20 μm diameter spots can be reliably patterned. For example, there can be patterning of a single capture antibody on the tip of each needle in the array. Multiplexing capability will be limited by the size of the active portion of the patch and the diameter, pitch, and density of the needles. As an example, for injection of needles into a vein (like a human cephalic vein or a rat lateral vein), then the active portion of the patch would be limited to 3-4 mm in width and 4-5 centimeters in length, thus allowing several thousand needles, fitting an array of at least 100 different antibodies (assuming a needle pitch of 100 μm).

In one example, the device can be used to focus on five cytokines which play a key role in Rheumatoid Arthritis, namely TNFα, IL1, IL4, IL10, and IL13.

TABLE 1

Relationship between pore diameter, number of pores per needle, signal-to-noise ratio (SNR) resulting from single antigen binding, and analyte acquisition time. Sensor width of 500 μm and analyte concentration of 10 fM is assumed.

| Pore Diameter (nm) | # of Pores per Needle | SNR of Single Antigen Binding | Time to Detect Single Antigen (s) | Analyte Acquisition Time |
|---|---|---|---|---|
| 20 | 25000 | 248 | — | — |
| 60 | 8333 | 30.5 | 150 | 4 hr |
| 100 | 5000 | 6 | 4 | 7 min |
| 200 | 2500 | 3 | 0.3 | 30 s |
| 300 | 1667 | 1 | 0.001 | 0.1 s |

Example 7

System Integration

Similar to previous work, the readout can be based on measuring the impedance between the top and bottom graphene electrode. Binding of analyte modulates the impedance by decreasing the ionic current passing across the nanopores (wells). The electronic readout can be performed using a lock-in-amplifier as the analog front-end circuitry. In some embodiments, since the patch itself is not being implanted and is removable, all of the electronic circuitry can be fabricated on the patch itself, which can be integrated with a flexible printed circuit board. No specialized readout need be required, and there need not be a need to develop new circuitry.

In some embodiments, the invention relates to an array of micro-needles with label-free sensors on top capable of full penetration through the skin to access the bloodstream.

In some embodiments, the invention relates to a wearable real-time continuous monitoring system with graphene based label-free sensing approach. A fully parametric analytical and computational COMSOL model of the graphene nano-sensor can be used to fully understand the design space and determine the optimum geometry and range of dimensions of the nano-sensor.

Graphene sensors of varying dimensions, such as pore diameter, insulator material, and insulator thickness can be fabricated to determine optimal device sensitivity. One can fabricate the sensors, for example, using the following process: 1) PDMS/PMMA transfer for deposition of first layer of graphene onto silicon dioxide. 2) Atomic layer deposition of silicon dioxide onto graphene. 3) PDMS/PMMA transfer for deposition of second layer of graphene onto silicon dioxide. 4) Atomic layer deposition of silicon dioxide onto graphene. 5) Using electron-beam lithography or photolithography with stepper aligner, one can pattern and etch an array of nanowells. One can use the commercial benchtop lock-in-amplifier to measure the impedance spectra of the graphene sensor to determine the optimum frequency of operation, which will be the region where the impedance is dominated by the pore resistance between the pair of graphene electrodes.

Surfaces can be functionalized for example, as follows: functionalize antibodies to the surface of the graphene electrode using PEG (Polyethylene Glycol)ylation via a polydopamine linker. The presence of the PEG layer will help to minimize non-specific adsorption of non-target antigens. Direct coupling of PEG to graphene can be achieved by capping the graphene (or reduced graphene oxide) with polydopamine via the simultaneous reduction of Graphene Oxide using dopamine hydrochloride and self-polymerization of the polydopamine. At weak pH, the oxidized catechol groups of the polydopamine can react with thiol- and amino-terminated polyethylene glycol (PEG) through the Michael addition and Michael addition/Schiff base reaction, respectively. With graphene oxide, these steps can also be performed pre-patterning, however, by doing so post-patterning, there are two advantages: avoid 1) extraneous filtration steps and 2) possibly damaging the functionalized GO sheets as a result of the photolithography process. The result is a PEG functionalized patterned RGO electrode. Then, to couple antibodies to the PEG layer, one can implement the Schott Nexterion H surface, which is a polyethylene glycol (PEG) hydrogel with reactive N-Hydroxysuccinimdyl ester (NETS) groups serving two purposes: 1) to enable protein immobilization and 2) to minimize non-specific binding and fouling of the electrode. One can use XPS, AFM, ellipsometry, and impedance spectroscopy to characterize the surface, layer by layer. A surface density of $1\times10^{12}$ antibodies/cm' is desirable. To quantify and characterize the coupling efficiency and probe density resulting from each protocol, one can use electrical impedance measurements. If NHS chemistry ends up resulting in sub-optimal capture antibody immobilization, then one can follow the approach of Korlach et al and use polyvinylphosphonic acid (PVPA) chemistry, which has been demonstrated to be successful for immobilizing proteins and enzymes in nano-scale wells.

In some embodiments, anti-IL4 antibody is functionalized on the surface of the sensor and detected IL4 label-free.

In some embodiments: sensitivity is at least 10 fM within 5 minutes; this can be done for 24 hours repeatedly; or both. The choice for 10 fM as the detection limit is that, cytokine levels are often present at picoMolar levels in serum.

In some embodiments, the invention relates to detecting the following panel of five inflammatory markers: TNF$\alpha$, IL1, IL4, IL10, and IL13. An array of five different capture antibodies (anti-TNF$\alpha$, anti-IL1, anti-IL4, anti-IL10, and anti-IL13) can be patterned onto the fabricated array of electronically addressable graphene sensors on a flat silicon dioxide substrate. To allow for lifetime extension of the sensor to enable a 24-hour-long assay, allocate at least 24 graphene sensors for each capture antibody; thus, the total array size can require at least 120 sensors. Cross-reactivity and non-specific binding occurring during the assay can be characterized. Various measures can be taken to minimize non-specific binding into the active sensing area, including use of PEG hydrogel linker layer on top of the graphene which serves to covalently bond the capture antibodies and minimize non-specific adsorption. Passivation of the sensor surface using blocking proteins such as rat serum albumin (because of assaying rat blood), and also casein can be tested.

In some embodiment, the invention relates to formation of label-free graphene sensor on micro-needle tip. An array of micro-needles can be fabricated with label-free sensors mounted on top, capable of minimally invasive penetration through the skin to access the blood stream to monitor cytokine concentrations in-vivo.

In some embodiments, there are fouling-resistant high aspect ratio polymeric micro-needles on a flexible substrate capable of penetrating through the skin with minimal discomfort and full access the bloodstream, with label-free graphene sensors fabricated on top of the polymeric micro-needle. In one aspect, this relates to optimizing the process for fabricating the needles and in another aspect, this relates to preventing fouling and non-specific adsorption of non-target inflammatory proteins.

In some embodiments, there is fabrication of a 15×15 array of polymer micro-needles and optimization of fabrication process for formation of addressable label-free graphene based sensors on the micro-needle tips. For example, to fully fabricate an array of 225 micro-needles with high aspect ratio (>2:1; 900 µm tall by 400 µm wide), with sensors mounted on top, which are fully functional and have the same electrical properties and sensitivity as the graphene sensors.

Needle structures can be fabricated using different materials, and their resilience to fouling tested by quantifying the level of non-specific adsorption of inflammatory molecules involved in the cascade of events leading to fouling of implantable devices. In the case of the microneedle array, the choice of needle dimensions can be guided by the potential application involving animals and humans. For example, the needle height required to penetrate the depth of the skin to access blood in the cephalic vein in the arm is approximately 800 μm, and the width required to minimize the pain associated with the venipuncture is 400 μm.

Some embodiments relate to high-aspect ratio (2:1) micro-needles fabricated using a series of different polymer materials including natural polymers such as collagen and amino-acid (e.g. Tyrosine) based polymers, synthetic polymers such as SU-8, and also coatings such as parylene. In some embodiments, the process recipe not only enables rigid high aspect ratio needles capable of penetrating through the skin to access the blood stream, but the processes are also compatible with formation of the label-free graphene sensors on the surfaces of the needles. In some embodiments, the invention relates to devices and processes for fabricating rigid needles with a height of 900 μm and a width of 400 μm.

Example 8

Formation of Label-Free Graphene Sensor onto Surface of Micro-Needle

Figure 14:
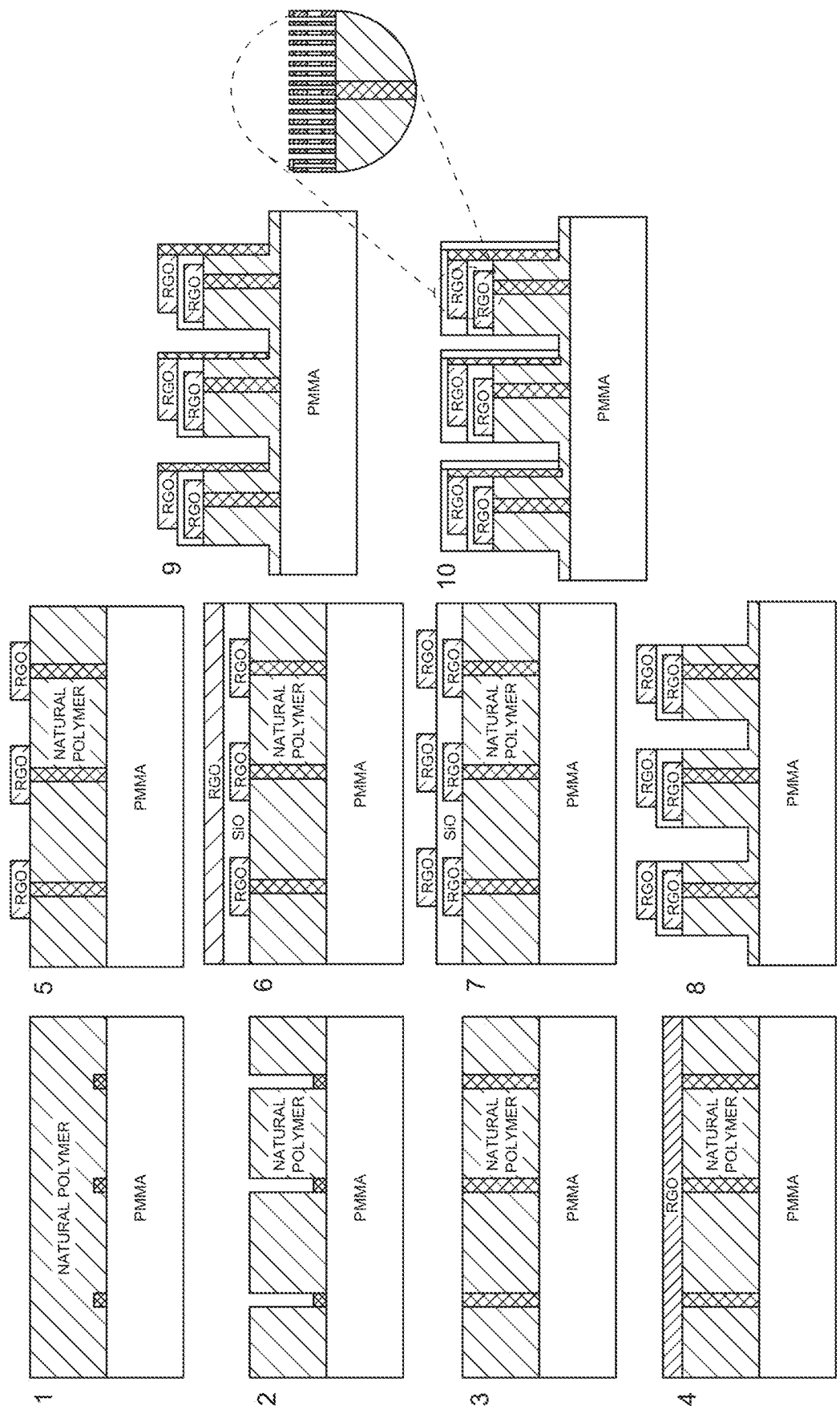
FIG. 14 illustrates a fabrication recipe for formation of graphene based label-free sensors onto polymer microneedle surface. Figure is not drawn to scale. The process includes the following procedures: On a thin-film PMMA layer, 1) micro-pattern copper electrodes, with a natural polymer spin-coated on top; 2) selectively etch the polymer using deep Reactive Ion Etching (RIE) or Ion Milling to create a via; 3) use copper electroplating to fill the via with metal to create an ohmic contact with the first graphene layer; 4)

After selecting a suitable material and process for fabrication of the micro-needle array, one can optimize the recipe for mounting the label-free sensor onto the tip of the needle. For example, see the process shown in FIG. 14, which includes the following procedures:

Form a PMMA layer onto a silicon substrate (as support). Micro-pattern a copper seed layer for electroplating. Deposit a polymer substrate layer above, which forms the body of the micro-needles (FIG. 14; step 1). Etch a via into the polymer layer exposing the copper seed layer (step 2), and use electroplating to fill in the via (step 3). This provides electrical access to the base graphene substrate of the label-free sensor. After having filled the via, deposit the graphene based (either graphene or reduced graphene oxide) electrode layer (step 4).

In some embodiments, CVD deposited graphene and also reduced graphene oxide are used as the electrode material. For graphene oxide one can use a modified dropcast technique, and for the pure monolayer of CVD graphene, PMMA/PDMS transfer of graphene can be used. The graphene oxide can be reduced either thermally or electrochemically, and then patterned using photolithography (FIG. 14, step 5). Atomic layer deposition can be used to deposit a thin layer of silicon dioxide (thickness range from 5 nm to 40 nm). A second layer of graphene (or graphene oxide) is deposited (step 6), and photo-patterned similar to the first layer (step 7). Next, use deep reactive ion etching to etch through the polymer substrate forming the micro-needle array (step 8). Angled metal deposition can be used to form gold traces at the side of the needle wall to be able to electrically access the top graphene based sensor electrode (step 9). Next, use atomic layer deposition (ALD) to deposit a top protective oxide layer to electrically insulate the top graphene electrode and the gold trace at the side of the needle. One can use electron-beam lithography or photolithography with a stepper aligner to etch nano-scale pores through the insulator, the top graphene electrode, and middle oxide layer (step 10).

Mechanical rigidity of the high aspect ratio needles, and the electrical properties of the graphene sensor, can be characterized to ensure that the performance is not compromised as a result of being formed on the tip of the needle. To ensure that sensor performance has not been compromised, one can perform impedance spectroscopy and voltammetry to ensure that the electrical characteristics are acceptable.

Example 9

In some aspects, the invention relates to fouling characterization and optimization routines. Optimum materials for biocompatibility and long-term in-vivo operation of the micro-needle array are determined. The Smart-patch is evaluated for fouling and non-specific adsorption of inflammatory molecules. Specifically, the devices are analyzed using both fluorescence microscopy and impedance spectroscopy to test for the non-specific adsorption of the following fluorescently labeled proteins: c3b, tumor necrosis factor (TNF-α), interleukin (IL)-1β, IL-6, and interferon-γ.

For example, each can be spiked into rat blood at a concentration of 100 nanoMolar. The results of the fluorescence assay facilitated optimizing the choice of polymer material for the micro-needles, which can minimize the binding of the key proteins, which are involved in triggering the inflammatory cascade, which ultimately results in electrode fouling.

In some embodiments, optimum material and chemistries are selected such that fluorescent levels after 24 hours of incubation of each of the markers are undetectable. Impedance levels from non-specific binding should be at least 10× less than the lowest levels of impedance modulation after a 24-hour measurement of one of the targeted inflammatory markers. In addition, certain anti-fouling robustness is inherent in that the fabrication of thousands of needles on a flexible substrate, allows significant room for redundancy and self-calibration through performing auto-correlation measurements between needles. Thus, it is possible to shut down sensors which have fallen outside of operational range, similar to techniques performed in the processor industry with memory, where faulty segments are shut down without the end-user having knowledge of it.

Example 10

Testing on Dry Stored-Samples

In some embodiments, sensor devices are functionalized, dried, and then used at a later time rather than having to do antibody immobilization during the experiment. The results presented in FIGS. 15A-15D and 16A-16D demonstrate that a dry, functionalized channel can effectively detect a target, suggesting that there may be no need to have a wet sensor.

FIGS. 15A-15D are plots of output voltage as a function of time illustrating sensor response after immobilization, drying, and then addition of test sample. FIG. 15A shows the sensor response to a negative control. FIG. 15B shows a zoomed-in region of FIG. 15A. FIG. 15C illustrates the sensor response to TNF-α, with FIG. 15D showing a zoomed-in region of FIG. 15C.

FIGS. 16A-16D are plots of output voltage as a function of time illustrating sensor response after immobilization, drying, 2-day storage, addition of test sample. FIG. 16A shows the sensor response to a negative control and FIG. 16B shows a zoomed-in region of FIG. 16A. FIG. 16C illustrates the sensor response to TNF-α, with FIG. 16D illustrating a zoomed-in portion of FIG. 16C.

Example 11

Multiplexing

In embodiments, the sensor can successfully detect target proteins in rat serum. For example, TNF-α, 116 and 114 have been shown to be detectable in serum comfortably. FIGS. 17A and 17B illustrate sensing of target protein 114 in rat serum. FIG. 17A is a plot of output voltage as a function of time illustrating sensor response to unspiked rat serum. FIG. 17B is a plot of output voltage of sensor response to rat serum spiked with 2 pM 114.

Example 12

Testing Directly in Spiked Blood

In some embodiments, the sensor can detect a target protein directly in spiked blood. For example, whole rat blood spiked with TNF-α was tested. FIGS. 18A and 18B are plots of output voltage as a function of time illustrating sensor response to unspiked whole blood (FIG. 18A) and whole blood spiked with TNF-α (FIG. 18B). Results shown in FIGS. 18A-18B suggest that blood cells do not interfere with the assay.

Example 13

Continuous Monitoring

In some embodiments, continuous monitoring is enabled by electronically unveiling sensors burning membranes allowing fluid to fall onto sensor. FIG. 19 is a plot of output voltage as a function of time illustrating sensor response for continuous monitoring including burning of membrane that initially covers the sensors.

As shown in FIG. 19, impedance of sensor can be visualized during the melting process of 10 seconds. Once the impedance drops significantly due to fluid falling onto sensor, the voltage (for melting membrane) is turned off. A signature exponential rise in impedance is observed at t=100 s.

Example 14

Integrated-Needle Sensor Insertion in Skin-Vein Phantom

In some embodiments, testing of electrical impedance properties of the integrated needle sensor in normal PBS buffer and also upon insertion confirms that the needles are not only mechanically resilient but sensors also maintain their electrical performance.

Example 15

Automated Analysis

In some embodiment, a computer-implemented process automatically analyzes sensor output data to detect target binding events. The process, which can be implemented in software, uses machine learning to automatically analyze the data and determine if an event is specific binding or a non-target event.

Automated analysis of impedance data presents a challenge. When a human operator looks at data, the operator can typically tell the difference between a real target binding event and the nontarget event. However, doing a simple before/after measurement will not always give the correct answer because of random drift and random baseline shifts due to addition of buffer. With their eyes, a human operator can simply tell which is a target event and which is non-target event. However, training a machine to also be able to accurately discern between the two types of events presents a challenge. A procedure for automatically processing and classifying data obtained with the impedance sensor is presented here.

Step 1 of the automatic process is feature extraction. Certain useful features of a voltage vs. time curve are illustrated in FIG. 20. Feature extraction can include the following procedures:
 a) Remove initial baseline shift
 b) Find maximum and minimum
 c) Fit beginning (decreasing part) to exponential decay, and fit end (increasing part) to power function Removing an initial baseline shift can be accomplished by calculating a difference vector (FIG. 21), which is similar to a derivative. In one example, the difference vector is employed to remove all data before the first point where the next 5000 differences are all smaller than 3.6 times the maximum of the first 200 differences.

FIG. 22A illustrates example output voltage data obtained with a sensor and FIG. 22B illustrates the same data with the baseline shift removed.

Fitting the sensor output data to exponential decay function can includes setting the minimum value as 0 (shift data down), determining the time constant τ=time between start value and start value*1/e and fitting shifted data to y=c*e(−t/τ), where −c=start value.

FIG. 23 illustrates the data of FIG. 22B and the exponential decay fit to the data.

Fitting to power function is illustrated in FIGS. 24 and 25. FIG. 24 illustrates specific binding data, here the protein data of FIG. 23, superimposed with a power fit and a linear fit at the end region (increasing region). As can be seen, the power fit is not appreciably different from the linear fit. FIG. 25 illustrates nonspecific binding data, here rat serum, superimposed with a power fit and a linear fit. As can be seen in the figure, the power fit approximates the data much better than the linear fit.

In Step 2, features are identified that can be used for classification. In one example, the features include (see FIG. 20):
 a) Time constant of exponential decay
 b) Exponent of power function
 c) Percent change from start to end
 d) Time between start and minimum (tmin)
 e) Time between start and maximum (tmax)

Note that tmin and tmax are calculated as fractions of the total experiment time.

An example feature vector that can be used in the automatic analysis includes the following variables:
 xstart=start time
 fstart=start value
 xmin=min time
 fmin=min value
 xmax=max time
 fmax=max value
 xend=end time
 fend=end value
 r=exponent of exponential decay function
 p=exponent of power function The above feature vector can be processed using cubic Support Vector Machine (SVM) analysis. For an example experimental data set, the SVM analysis is performed where the classification model is trained on 21 experiments and tested on other 33. The results indicate that the classification model's predictions are 100% accurate.

Example 16

Mouse Cytokine Titration Results

FIGS. 26A-26D illustrate mouse cytokine titration curves in spiked serum and comparison with Luminex, which is considered to be a gold standard. In FIGS. 26A-26D, each plot provides titration curves for a platform to platform comparison of nanowell impedance sensor and Luminex assay over a wide range of concentrations in mouse serum sample spiked with (FIG. 26A) TNF-α, (FIG. 26B) IL6, (FIG. 26C) IL10, and (FIG. 26D) CXCL2. Values on Y axis to the left represent percentage voltage change in nanowell impedance sensor as a function of target cytokine concentration. Values on Y axis to the right represent Luminex count as a function of target cytokine concentration.

Example 17

Demonstration of Needle-Sensor Functionality Post-Insertion

FIGS. 27A-27D illustrate needle-sensor functionality post insertion of the sensor into a skin phantom. FIGS. 27A, 27B, and 27D show lock-in amplification data at 1 MHz. FIG. 27C illustrates a sensor on glass needle that is inserted through a vertical skin phantom after antibody immobilization. In order to test the robustness of antibody-functionalized sensor on glass needle: before adding target protein, the sensor was inserted through a vertical skin phantom and then retrieved back to the test fluidic cell. Sensor output response data is shown in FIG. 27A. Pre-insertion: the immobilization of antibody (e.g., anti-TNF-α) on sensor surface caused an increase in impedance as expected, which is visible as a drop in the output voltage (~1.9%) in FIG. 27B. Post-insertion: specific binding of target protein (TNF-α) to antibody resulted in an increase in impedance as expected, which is visible as a drop in the output voltage (~1%) in FIG. 27D.

Example 18

Transdermal Insertion Tests of Sensor into Mouse Muscle

FIG. 28A illustrates manual insertion of a needle sensor by holding the sensor connector with tweezers. The sensor is inserted in the left rear limb muscle by piercing through intact skin. FIG. 28B shows the sensor inserted into the muscle facing front. FIG. 28C shows the sensor inserted and rotated, facing back. The transdermal insertion tests confirmed that is it possible to manually insert the sensor into mouse muscle tissue by directly piercing through the skin (the mouse was sacrificed 20 min before the test).

Example 19

Multiwell Plate of Nanowell Array Sensors for Label-Free Detection of Cytokines

Measurement of various specific proteins in body fluids can be a key component of continuous health monitoring. Common techniques for protein quantification usually rely on labeling and optical fluorescence. As an alternative approach, electrochemical impedance analyses have been recognized as a powerful tool for different types of sensor applications due to significant advantages, such as inherent simplicity, rapid response, high sensitivity, and low cost.

Electrochemical impedance spectroscopy (EIS) based sensors benefit from ease of miniaturization, reliability in detecting biomarkers, and label-free operation. These sensors are particularly well-suited to detect binding events on the transducer surface, which makes them ideal candidates for detection of deoxyribonucleic acid (DNA) and proteins.

Multiwell plate assays present suitable conditions for screening biological or chemical libraries in static fluid environments in which many samples can be analyzed in parallel. These platforms can be combined with impedance-based biosensors to improve both the sensitivity and efficiency, since it promotes attachment of antibody to the electrode surface and enables simultaneous detection of different analytes by immobilizing their respective ligands on separate electrodes. Moreover, these assays can provide real-time analysis of cells in culture without the need for enzymatic stripping, fluorescent dyes, fixatives, or other perturbations.

Here, the nanowell array electrodes are designed as a platform to carry out the dual functions of electric field antibody immobilization and providing a highly sensitive EIS platform. The electric field focusing is employed to immobilize probe antibody more uniformly to minimize the unwanted nonspecific binding or aggregation of antibody molecules inside the nanowells. A wafer-scale sensing configuration with 40-nm-electrode gap is described. The nanowell array functionalized biosensor demonstrates a dynamic range of 10-500 ng/l for tumor necrosis factor alpha (TNF-α) in mouse serum with a limit of detection of 10 ng/l. Robust performance through repeated testing in mouse serum is determined by extracting a calibration curve. Additional details of the nanowell array sensor, method of fabrication, and experimental data are described in S. R. Mahmoodi, P. Xie, M. Allen and M. Javanmard, "Multiwell Plate Impedance Analysis of a Nanowell Array Sensor for Label-Free Detection of Cytokines in Mouse Serum," in IEEE Sensors Letters, vol. 4, no. 2, pp. 1-4, February 2020, Art no. 4500104, the entire teachings of which are incorporated herein by reference.

Nanowell array biosensors significantly improve label-free detection by providing highly sensitive analyses. In the example embodiment described here, the sensor 510 comprises a 20×20 µm$^2$ overlap area at the tip of the two confronting electrodes 512, 514 with 25 individual nanowells 520 (FIG. 29). The wells are arranged in a 5×5 rectangular pattern (e.g., nanowell array) 522, but other arrangements may be used. The sensor is fabricated by patterning gold electrodes on a glass substrate. Connection pads 515 are fabricated on opposing sides of the chip 500 with traces leading to the center of the chip. The two electrodes overlap with each other and are separated by a thin aluminum oxide layer. The micropatterned holes expose the bottom electrode to the test solution and the probe antibody of the target analyte, here antibody of tumor necrosis factor alpha (anti-TNF-α), can be immobilized inside the nanowells by the electric field focusing.

FIG. 29 shows the assembled multiwell device 500 and schematic views of a nanowell array sensor 510, comprising a pair of gold electrodes 512, 514 separated by a 40-nm insulator layer 518. The bottom electrode 514 is formed on a glass substrate 528. The top electrode 512 is covered by another insulator layer 530. The entire multiwell plate chip 500 includes 28 sensors 510 in separate polydimethylsiloxane (PDMS) wells 505. Binding of target antigen 526 modulates the impedance between the electrodes, resulting in a change in the impedance spectra due to partial occlusion of charges passing between the two electrodes. Higher salt concentration results in larger current, and thus in higher signal power corresponding to larger changes in current due to protein binding, making the sensor ideal for quantification of proteins in high salt content matrices, such as serum.

In the example multiwell chip shown in FIG. 29, there are 28 wells 505 formed in PDMS and arranged in a 4×7 grid, each well including one nanowell sensor 510, each nanowell sensor comprising a 5×5 nanowell array 522, each nanowell having a diameter of 2 µm. In some embodiments, each nanowell sensor includes the same antibody, such that each sensor is configured to detect the same target analyte. In some embodiments, a portion of the nanowell sensors includes one antibody and another portion of the nanowell sensors includes another (e.g., different) antibody. For example, the wells can be arranged in two or more rows, wherein each row comprises nanowell sensors that include the same antibody, to detect the same target analyte in each row. In some embodiments, one or more nanowell sensors may be positioned in each well. For example, at least two nanowell sensors may be positioned in a well. In some embodiments, the multiwell chip can include more than 28 wells. For example, the multiwell chip can include 96 wells or 384 wells.

In the nanowell array sensor, most of the gold electrode area is covered with an aluminum oxide layer such that only a limited surface of the electrodes is exposed to the test solution inside the nanowells. Therefore, this geometry limits the amount of probe antibody molecules inside the nanowell and thus can provide more sensitive detection of surface binding events. Furthermore, the small surface of the electrodes can improve the sensitivity by concentrating the electric field into a small volume inside the nanowells. Moreover, electric field immobilization can align antibody molecules along the electric field to enhance the sensor performance.

The processing steps of the sensor structure are described and, in some aspects, are similar to the fabrication processes described with respect to sensors of FIGS. 1 and 7A-7C. First, a bare fused silica wafer (University Wafer, South Boston, MA, USA) was cleaned by oxygen plasma. Then, a layer of 150-nm thick gold was deposited on the wafer by e-beam evaporation and patterned by lift-off, yielding the bottom layer electrode. Atomic layer deposition (ALD) was used to deposit a 40-nm-aluminum-oxide film as an inter-electrode insulator. The top gold electrode, the interconnecting lines, and the connection pads (150 nm) were patterned using the same method as for the bottom layer electrode. Five-nm layers of chromium and aluminum were coated by e-beam and thermal evaporation, respectively, to enhance the adhesion of the gold electrodes and the aluminum oxide layer to their corresponding substrates. Next, another 40-nm passivation layer of aluminum oxide was deposited on top of this structure by ALD. Finally, the nanowells were patterned in the overlapping part of the two electrodes and etched by ion milling to fabricate the nanowell array. Gold connection pads of the bottom electrodes were protected by small pieces of Kapton tape during the entire fabrication procedure. Thereafter, a PDMS block with 28 holes was bonded to the wafer by oxygen plasma treatment to fluidically isolate each sensor pairs and to create the multiwell plate design (see FIG. 29).

Described is a nanowell array impedance sensor for label-free detection of cytokines and other biomarkers. The electrode structure includes two opposing electrodes such that the overlapping region of the two electrodes is separated by a thin oxide layer and micropatterned with holes that expose the bottom electrode to solution. By monitoring the impedance across the electrodes after sensor functionalization with antibody, one can record the EIS measurements at each stage of the fluid additions. Fitting the data to Randles' equivalent circuit model demonstrates that reliable detection of TNF-α is possible at a dynamic range between 10 and 500 ng/l. Negative control measurements can be performed using blank mouse serum and PBS to ensure that sensor fouling does not result in false positive signals.

Nanowell array sensors, such as illustrated in FIG. 29, are particularly useful for rapid, point-of-care detection of cytokines or other small molecules. For example, nanowell sensor arrays can be used detect and/or monitor 'cytokine storm' in patients suffering from respiratory virus infections, such as Corona Virus Disease 2019 (COVID-19). It is thought that in some COVID-19 patients, the patient's immune system is overreacting to the virus. The problem, known broadly as a 'cytokine storm, can happen when the immune system triggers a runaway response, e.g., releasing too many cytokines, such as interleukin 6 (IL-6), which causes more damage to its own cells than to the invader (e.g., virus) it is trying to fight.

In some embodiments, a companion kit for monitoring 'cytokine storm' in COVID-19 patients includes one or more nanowell array sensors. The one or more nanowell sensors can be positioned at the bottom of one or more mm-sized wells, such as described above and illustrated in FIG. 29.

Example 20

Serological Testing

In some embodiments, one or more nanowell sensors are employed in serology testing, where the target analyte is an antibody. For example, one or more proteins/peptides (e.g., antigens) are conjugated in the nanowells of the sensor(s) for detecting an antibody (or antibodies) of interest in a blood sample. Serological detection of antibodies (e.g., IgG and IgM) is useful for detecting exposure to an infection and/or immunity to an infection, such as influenza and COVID-19.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A sensor for label-free detection of a target analyte in a sample, the sensor comprising:
   a) a substrate and a pair of conducting electrodes, one of the electrodes of the pair being a base electrode disposed on the substrate, the other of the electrodes of the pair being an upper electrode, the electrodes being parallel plates;
   b) an insulator disposed between the electrodes and supporting the upper electrode;
   c) an array of wells defined by through holes in the upper electrode and the insulator, the base electrode providing a lower surface of each of the wells of the array, the wells configured to receive a sample including a target analyte, an impedance between the electrodes being modulated by the target analyte, when present in the sample received in the wells, the modulated impedance being indicative of the concentration of the target analyte in the sample; and
   d) a needle-shaped tip at a portion of the substrate.

2. The sensor of claim 1, wherein the wells are configured to bind the target analyte.

3. The sensor of claim 2, wherein the wells include antibodies immobilized inside the wells, the antibodies configured to bind the target analyte.

4. The sensor of claim 3, wherein the target analyte is a protein found in blood.

5. The sensor of claim 1, wherein the electrodes are gold electrodes and the insulator comprises aluminum oxide.

6. The sensor of claim 1, further including a protective layer covering the upper electrode that defines the array of wells.

7. The sensor of claim 6, wherein the substrate comprises a material configured to flex.

8. The sensor of claim 6, wherein the protective layer covers portions of the wells and further comprising circuitry configured to selectively melt away the protective layer by applying a voltage to the protective layer to sequentially unveil the portions of the wells for continuous monitoring of the analyte.

9. The sensor of claim 1, wherein the diameter of each well is in the range of about 1 micrometer to about 4 micrometers.

10. The sensor of claim 1, wherein the wells are arranged in a regularly spaced array.

11. The sensor of claim 1, further including circuitry coupled to the electrodes, the circuitry applying an electrical voltage to the sample in the wells via the electrodes and measuring a current via the electrodes in response to the voltage applied, the modulated impedance between electrodes being determined as a function of the voltage applied and the current measured.

12. The sensor of claim 11, wherein the circuit is configured to apply the voltage as a time varying signal, and wherein the modulated impedance is determined at a frequency in the range of about 50 kHz to about 10 Mhz.

13. The sensor of claim 12, wherein the modulated impedance is determined at about 1 MHz.

14. The sensor of claim 11, wherein the circuitry includes a lock-in amplifier.

15. A transcutaneous impedance sensor apparatus for label-free, in-situ detection of a target analyte, the sensor apparatus comprising:
   a) a sensor comprising:
      i) a substrate comprising a material configured to flex;
      ii) a pair of conducting electrodes, one of the electrodes of the pair being a base electrode disposed on the substrate and the other of the electrodes of the pair being an upper electrode, the electrodes being parallel plates;
      iii) an insulator disposed between the electrodes;
      iv) an array of wells defined by through holes in the upper electrode and the insulator, the base electrode providing a lower surface of each of the wells of the array, the wells configured to receive a biological fluid sample including a target analyte;
      v) antibodies immobilized inside the wells, wherein binding of the target analyte, when present in the biological fluid sample received in the wells, modulates an impedance between the electrodes, the modulated impedance being indicative of the concentration of the target analyte in the biological fluid sample; and
   b) an insertion device to insert the sensor through skin into a biological body, the insertion device including a needle-shaped tip.

16. The sensor apparatus of claim 15, wherein the insertion device and the sensor are arrangeable to position the array of wells near the needle-shaped tip.

17. The sensor apparatus of claim 15, wherein the antibodies are configured to bind a target analyte that is a cytokine.

* * * * *